(12) United States Patent
Ramachandran et al.

(10) Patent No.: US 7,418,767 B2
(45) Date of Patent: Sep. 2, 2008

(54) AUTOMATIC FIBER PROCESSING SYSTEM INCLUDING METHOD AND APPARATUS FOR PRODUCING END-ALIGNED FIBER SAMPLES

(75) Inventors: Shekaripuram Narayanaswamy Ramachandran, Coimbatore (IN); Varadarajan Srinivasan, Coimbatore (IN); Mariappan Anbarasan, Coimbatore (IN)

(73) Assignee: Premier Evolvics Pvt. Ltd., Coimbatore (IN)

( * ) Notice: Subject to any disclaimer, the term of this patent is extended or adjusted under 35 U.S.C. 154(b) by 413 days.

(21) Appl. No.: 10/549,974

(22) PCT Filed: Mar. 28, 2003

(86) PCT No.: PCT/IB03/01805

§ 371 (c)(1),
(2), (4) Date: Sep. 20, 2005

(87) PCT Pub. No.: WO2004/086097

PCT Pub. Date: Oct. 7, 2004

(65) Prior Publication Data

US 2006/0179932 A1    Aug. 17, 2006

(51) Int. Cl.
*D01G 21/00*    (2006.01)
(52) U.S. Cl. ......................................... 19/65 A; 19/215
(58) Field of Classification Search ............... 19/66 CC, 19/65 R, 66 R, 65 A, 115 R, 200, 202–205, 19/215; 73/159, 160, 828, 830; 356/429
See application file for complete search history.

(56) References Cited

U.S. PATENT DOCUMENTS

| | | | |
|---|---|---|---|
| 5,178,007 A | 1/1993 | Ghorashi et al. | |
| 5,367,747 A | 11/1994 | Shofner et al. | |
| 5,457,851 A | 10/1995 | Mondini | |
| 5,483,844 A | 1/1996 | Shofner et al. | |
| 5,537,868 A | 7/1996 | Shofner et al. | |
| 5,890,264 A | 4/1999 | Shofner et al. | |
| 5,892,142 A | 4/1999 | Ghorashi et al. | |
| 5,907,394 A | 5/1999 | Ghorashi et al. | |
| 5,943,907 A | 8/1999 | Ghorashi et al. | |
| 6,085,584 A * | 7/2000 | Ramachandran et al. | 73/159 |
| 6,098,454 A | 8/2000 | Ghorashi et al. | |
| 6,112,131 A | 8/2000 | Ghorashi et al. | |
| 6,598,267 B2 | 7/2003 | Shofner et al. | |

* cited by examiner

*Primary Examiner*—Shaun R Hurley
(74) *Attorney, Agent, or Firm*—Dority & Manning, P.A.

(57) ABSTRACT

The apparatus for the preparation of an end-aligned fiber sample comprises an array of fiber combs, a first drive unit, a fiber collection device connected to the first drive unit, a suction device, a detection device and a control unit to control each of the foregoing components. The method for preparing an end-aligned fiber sample uses the control unit to operate each of the foregoing components to prepare an end-aligned fiber sample. The apparatus can be combined with testing units for testing the end-aligned fiber samples. One of the testing units can test for short fiber content. The testing for short fiber content also can employ the detection device of the apparatus.

29 Claims, 17 Drawing Sheets

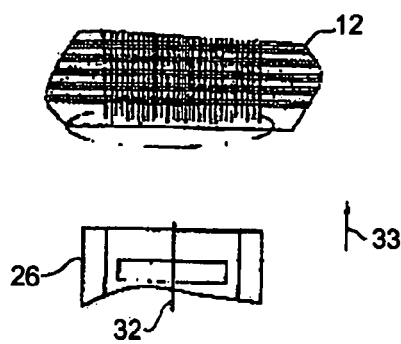
FIG. 4A-n
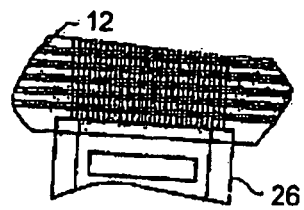
FIG. 4B-n
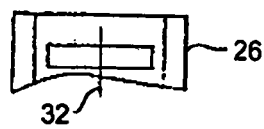
FIG. 4D-n
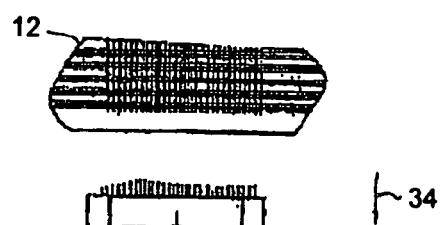
FIG. 4C-N
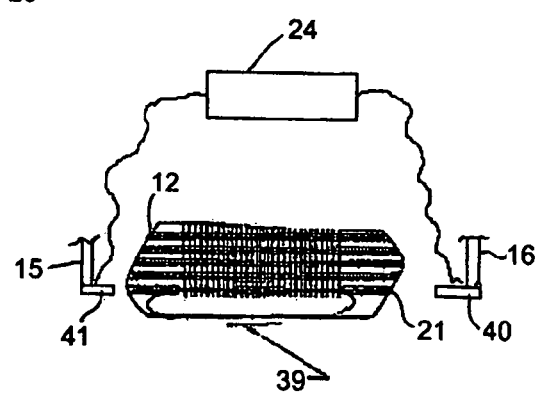
FIG. 4E-n

AUTOMATIC FIBER PROCESSING SYSTEM INCLUDING METHOD AND APPARATUS FOR PRODUCING END-ALIGNED FIBER SAMPLES

CROSS-REFERENCE TO RELATED APPLICATIONS

N/A

STATEMENT REGARDING FEDERALLY SPONSORED RESEARCH OR DEVELOPMENT

N/A

BACKGROUND OF THE INVENTION

The present invention relates to automatic fiber processing. More particularly, the invention relates to method and apparatus for preparing fiber samples and measurement of fiber characteristics from those samples.

When processing natural fibers, especially cotton, ensuring the desired quality of the fibers remains one of the most important considerations. The market value of the fibers depends on their quality. To this end, it is necessary to conduct constant monitoring of the raw fiber product that serves as the feedstock to be processed. Such monitoring typically occurs by means of testing that is performed on samples taken at random from the raw fed product before it is introduced into the process.

The testing aims to determine quality factors such as length, length uniformity, strength, elongation, trash, color, micronaire and fineness. Different efforts have been made to automate the standardized tests that measure these quality factors. Some of these efforts are detailed in U.S. Pat. No. 5,167,150 (tension elongation and cross-sectional properties); U.S. Pat. No. 5,907,394 (fiber strength); U.S. Pat. No. 6,040,905 (fiber color grading); U.S. Pat. No. 6,098,454 (moisture content, trash content, micronaire, maturity, length distribution, strength, elongation); which patents are hereby incorporated herein by this reference. However, the preparation of the fiber samples for these tests was normally carried out by hand or in a less than fully automated manner.

Typical steps involved in obtaining the fiber characteristics from a fiber bundle, such as a cotton sample, include the gathering of a specimen sample from a larger amount of fibers, preparing the specimen for testing and then performing a number of tests upon the prepared specimen. The step of preparing of the specimen sample for testing may involve carding and brushing of the specimen fibers. The form of the test specimen may vary depending upon the fiber characteristics that are measured. The tests performed upon such specimen may measure characteristics such as length, length uniformity, strength, elongation, micronaire, fineness, color and trash. The measured characteristics may also further be used for deriving additional parameters through calculations, regressions or such other means. Such characteristics may include those that are not easily measured directly, such as proportion of short fibers, maturity, predicted yarn parameters, consolidated fiber quality indices, etc.

Among the several pieces of equipment capable of measuring fiber quality characteristics at high speed are those manufactured by Premier Polytronics, India, which is the owner of this application, and Zellweger Uster, USA. In such systems, the measurement of length is carried out on a tapered beard sub-sample, which is obtained by gripping the fibers at a random catching point. See U.S. Pat. No. 6,085,584, which is hereby incorporated herein by this reference. In such cases, the sample contains fibers arranged so that the direction of each fiber's length extension is parallel to the direction of each other fiber's length extension. However, the ends of these fibers are not aligned with each other in a straight line along either opposite edge of the specimen.

Such a specimen broadly represents the manner in which the fibers are arranged in fiber assemblies such as sliver, roving and yarn. Hence, the length measurements made with such a sample are widely used for optimizing the machinery parameters, particularly the roller settings. But these methods do not give a satisfactory estimate of the short fiber content in the sample.

A second known method of measuring short fiber characteristics is by scanning individual fibers, such as is done in Zellweger Uster's AFIS. See U.S. Pat. No. 5,270,787, which is hereby incorporated herein by this refrence. However, such a method uses a fixed upper length limit for defining the short fibers. This is likely to lead to incorrect interpretation of the results with certain varieties of cotton. Additional disadvantages inherent in this method and apparatus include the non-linear motion of the fiber across the sensor, the inability to obtain data from fibers that are not suitably arranged for measurement, and the overestimation of the fiber length that occurs upon the overlapping of more than one fiber.

A reliable estimate of the short fiber content can be obtained only if the tests are performed on a sample that has one end of each of the fibers aligned with the ends of the other fibers. With such an end-aligned sample (FIG. 2B for example), the length of the fiber extending from the aligned end represents the full length of the fibers, and so the shorter fibers can be distinguished easily from the longer fibers. This method is used in the conventional manual methods of length measurement such as the Shirley Comb Sorter or the Baer-Sorter array method.

Detailed explanation of the manual testing procedure with a Shirley CombSorter or the BaerSorter array is given in the British Standards Handbook. An extract of the British Standards Handbook can be found in the Butterworths Publication "Principles of Textile Testing," by J. E. Booth. A brief description of the procedure is given below.

In the BaerSorter method, the tester uses a bed of combs, which control the fibers and enable the sample to be fractionalized into length groups. A grip, an aluminum depressor and a blunt needle are used manually by the tester to manipulate the fibers. From a sample of about 20 grams, the test sub-sample is prepared by carefully drawing and doubling fiber tufts several times until the fibers are straightened along their lengths, which in turn are rendered parallel to each other. During this preparation process, fibers are pulled out in tufts of successively shorter lengths by means of the grip, the longest first by successively dropping the combs as required. The fibers are combed, straightened and laid down on a velvet pad with the straight edge against a marked line in decreasing order of fiber length. The outline produced by the upper ends of the fibers is similar to a cumulative frequency diagram. Provided that the fibers are evenly spaced on the velvet pad, distances along the base line are proportional to the number of fibers. The shape of the distribution provides preliminary information on the length characteristics. A more detailed analysis can be performed by transferring the shape to a tracing. With this tracing, detailed information such as short fiber percentage, effective length, etc., are obtained by various geometrical constructions.

Though manual, time-consuming and labor intensive, the BaerSorter method is still considered to be the best among the available methods for measurement of short fibers. However, while these manual methods have proved to be useful reference measures for other length measuring equipment, these manual methods themselves cannot be used for regular measurement due to the unacceptable time required for performing such measurements.

OBJECTS AND SUMMARY OF THE INVENTION

Considering the above situation, it is a principal object of the present invention to provide a fiber testing apparatus capable of automatically providing end-aligned fiber samples for testing length characteristics at speeds compatible with high volume testing methods.

It is another principal object of the present invention to provide a fiber testing apparatus capable of automatically providing end-aligned fiber samples and testing the samples to determine a reliable estimate of the short fiber content of the samples.

It is also a principal object of the present invention to eliminate the known disadvantages in a fiber testing system for the automatic determination of material parameters. The system should include the automatic preparation of a sample composed of end-aligned fibers. The material parameters are to be determinable with a high repeating accuracy as well as precision and in as little time as possible. The transport mechanism is to be simple, maintenance friendly and inexpensive.

The invention includes a method and apparatus for preparation of end-aligned fiber samples, both one-at-a time and multiple samples prepared simultaneously. Alterative embodiments can include method and apparatus for measurement of fiber length and thereby measurement of the proportion of short fibers. In other alternative embodiments, the foregoing can be effected desirably in combination with measurement of other fiber characteristics in a known or improved means.

These objects and others are achieved by the various embodiments of the invention that are defined in the patent claims.

The accompanying drawings, which are incorporated in and constitute a part of this specification, illustrate at least one presently preferred embodiment of the invention as well as some alternative embodiments. These drawings, together with the description, serve to explain the principles of the invention but by no means are intended to be exhaustive of all of the possible manifestations of the invention.

BRIEF DESCRIPTION OF THE DRAWINGS

FIG. 4A-1 schematically shows a top plan view of portions of components of an embodiment of the present invention.

FIG. 4B-1 schematically shows a top plan view of portions of components of an embodiment of the present invention shown in FIG. 4A-1.

FIG. 4C-1 schematically shows a top plan view of portions of components of an embodiment of the present invention shown in FIG. 4B-1.

FIG. 4D-1 schematically shows a top plan view of a portion of a component of an embodiment of the present invention shown in FIG. 4C-1.

FIG. 4A-2 schematically shows a top plan view of portions of components of an embodiment of the present invention.

FIG. 4B-2 schematically shows a top plan view of portions of components of an embodiment of the present invention shown in FIG. 4A-2.

FIG. 4C-2 schematically shows a top plan view of portions of components of an embodiment of the present invention shown in FIG. 4B-2.

FIG. 4D-2 schematically shows a top plan view of a portion of a component of an embodiment of the present invention shown in FIG. 4C-2.

FIG. 4A-$n$ schematically shows a top plan view of portions of components of an embodiment of the present invention.

FIG. 4B-$n$ schematically shows a top plan view of portions of components of an embodiment of the present invention shown in FIG. 4A-$n$.

FIG. 4C-$n$ schematically shows a top plan view of portions of components of an embodiment of the present invention shown in FIG. 4B-$n$.

FIG. 4D-$n$ schematically shows a top plan view of a portion of a component of an embodiment of the present invention shown in FIG. 4C-$n$.

FIG. 4E-$n$ schematically shows a top plan view of portions of components of an embodiment of the present invention shown in FIG. 4A-$n$.

DETAILED DESCRIPTION OF THE PREFERRED EMBODIMENTS

Reference now will be made in detail to the presently preferred embodiments of the invention, examples of which are illustrated in the accompanying drawings. Each example is provided by way of explanation of the invention, which is not restricted to the specifics of the examples. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention include such modifications and variations as come within the scope of the appended claims and their equivalents. The same numerals are assigned to the same components throughout the drawings and description. A similar numbering scheme is followed to indicate similar components.

Initially, the apparatus for automatically preparing an end-aligned fiber sample will be described together with the methodology performed by this apparatus. Then, the description will explain how other apparatus and methodology can desirably be combined with the end-aligned fiber preparation apparatus and automated methodology.

Figure 1:
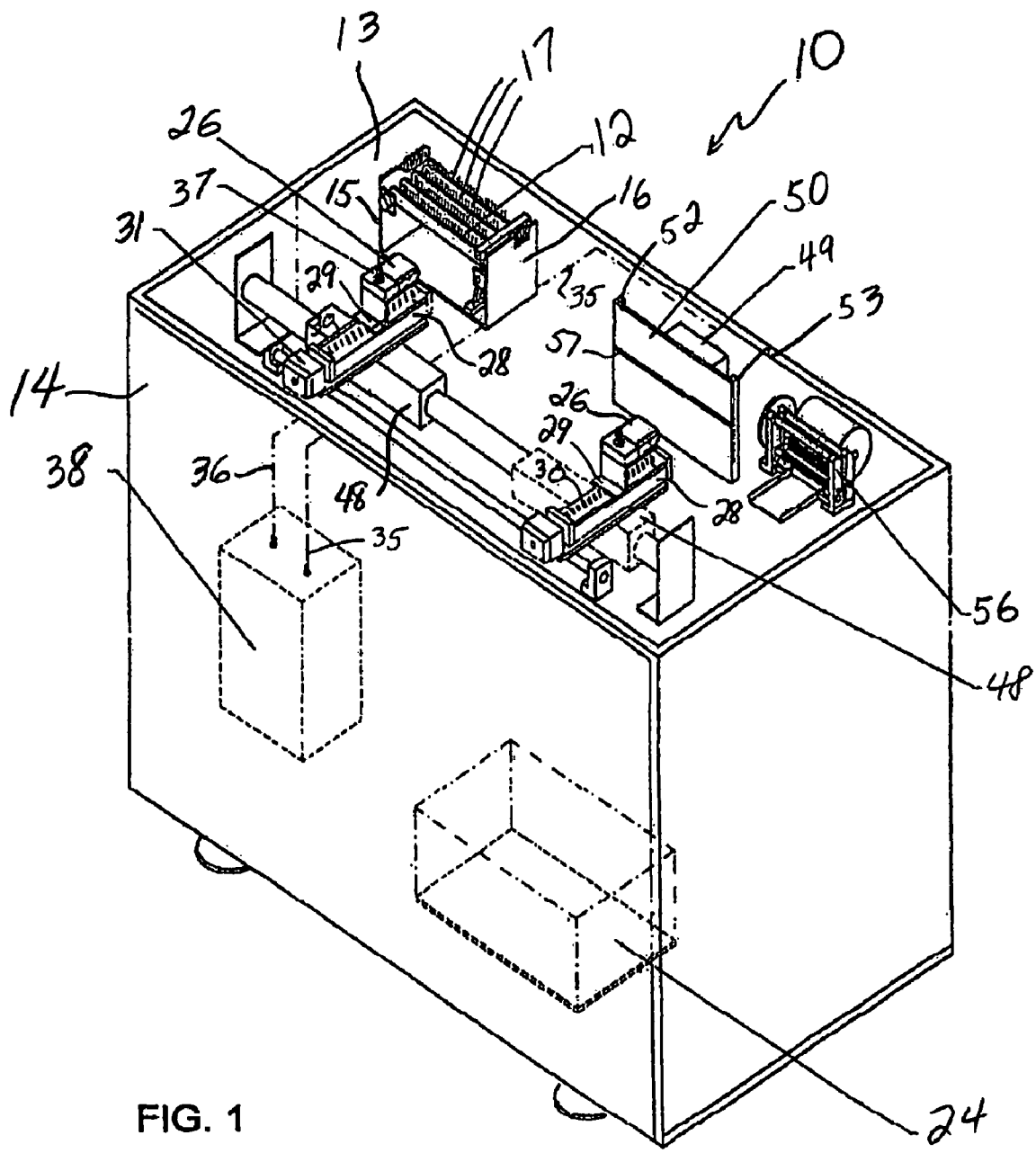
FIG. 1 shows an elevated perspective view of an embodiment of the apparatus of the present invention.
Figure 5B:
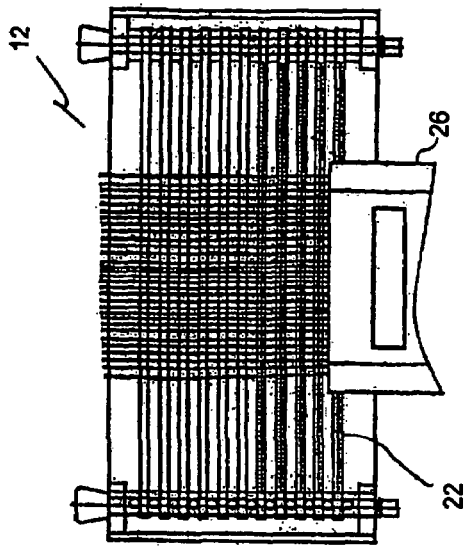
FIG. 5B schematically shows a top plan view of portions of components of an embodiment of the present invention shown in FIG. 5A.

FIG. 1 shows an elevated three-dimensional perspective view of an embodiment of an automatic fiber processing system 10 that includes an apparatus for preparation of an end-aligned fiber sample according to the invention. In accordance with the present invention, the apparatus for aligning one end of a fiber sample before testing includes an array of aligned fiber combs. As embodied herein and shown in FIG. 1 for example, a fiber comb array 12 is disposed and connected to a tabletop 13 of a cabinet 14. As embodied herein and shown in FIGS. 3A and 3B for example, the fiber comb array 12 includes a rigid frame 11 having opposed vertical sidewalls 15, 16. As shown in FIG. 1, the sidewalls 15, 16 support respective opposite ends of a plurality of fiber combs 17 lined up side-by-side and parallel to each other along their respective lengths. As shown in the top plan view of FIG. 5A for example, each comb 17 is arranged so that its length direction is parallel to the length direction of each other comb 17. The individual fiber combs 17 are held in the array 12 and supported between the two side walls 15, 16.

Figure 3A:
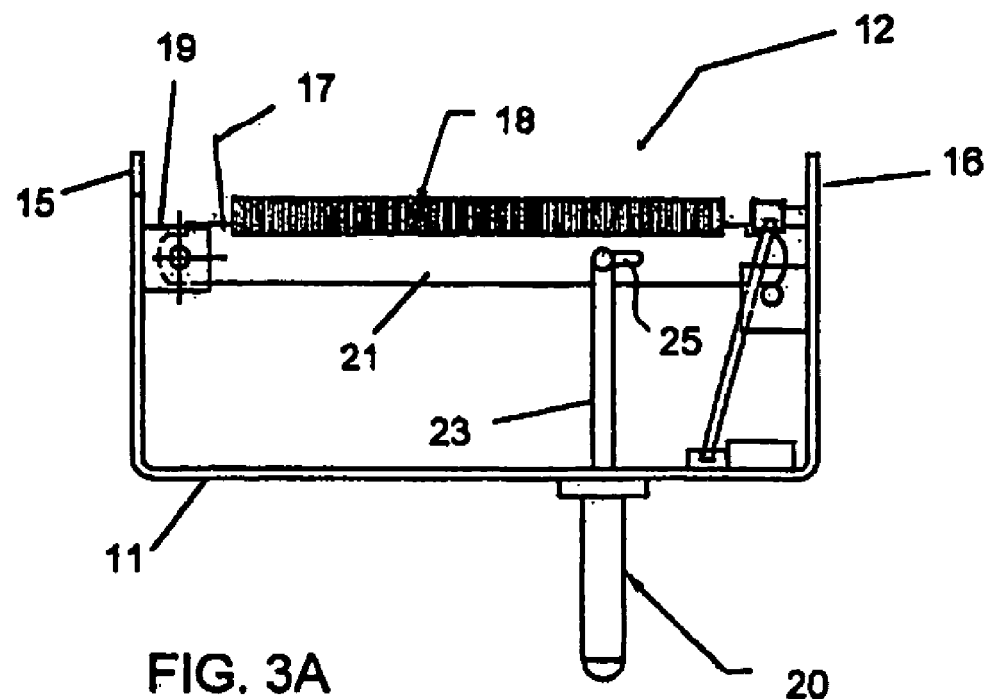
FIG. 3A shows a front plan view of a fiber comb array in which the front comb is disposed in its raised position at the same height as all of the other combs in the array.

As shown in FIG. 3A, the upper edge of each comb 17 includes a plurality of upwardly projecting needles 18 or teeth that are spaced apart along the length of the comb. The sets of needles 18 in the array of fiber combs 17 are used to retain the fiber sample during the process of the end alignment. The needles 18 additionally can be used to perform a partial combing action while the fiber sample is being collected. The spacing between adjacent needles 18 or teeth desirably is uniform and on the order of about twice the anticipated maximum thickness of the fibers that are to be carried by the array 12 of fiber combs 17. The array 12 of fiber combs 17 is configured to receive a given fiber sample resting with the direction of length extension of the fiber strands in the sample generally disposed transversely to the length direction of the fiber combs.

Figure 3B:
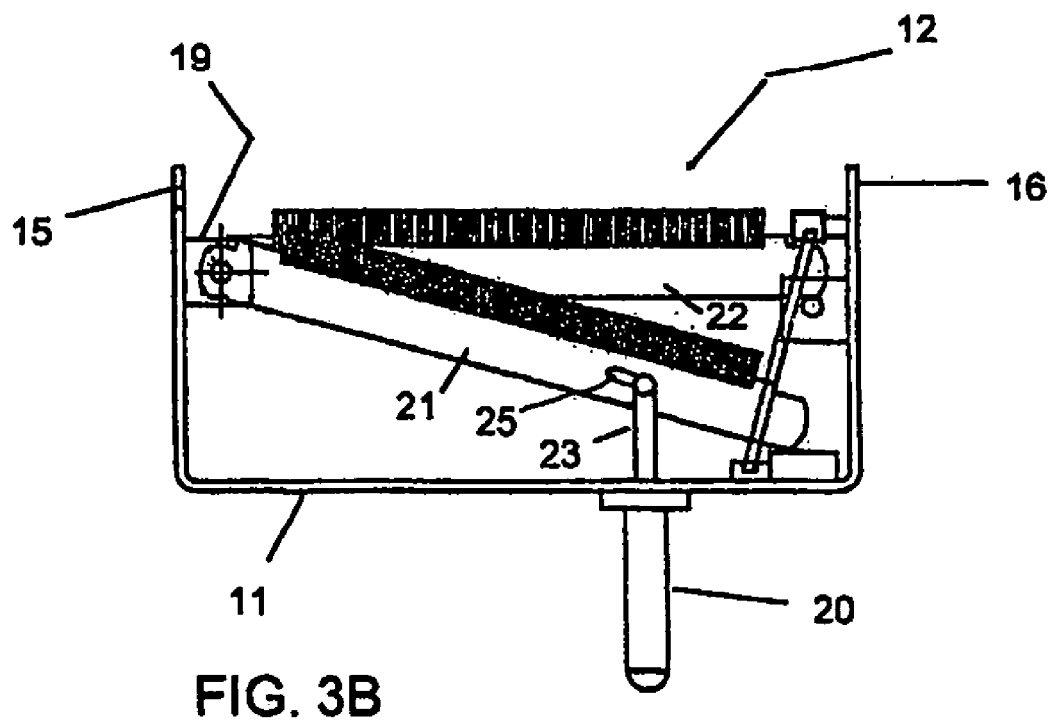
FIG. 3B shows a front plan view of a fiber comb array in which the front comb is disposed in its lowered position that is beneath the height of the other combs in the array.

The array 12 of fiber combs includes at least a first fiber comb and a second fiber comb disposed parallel to and behind the first fiber comb. As schematically shown in FIG. 3B for example, a front fiber comb 21 forms a first fiber comb 21 that is disposed in front of a second fiber comb 22. One end of front fiber comb 21 is pivotally connected to a flange 19 that is attached to one sidewall 15 of the frame 11 of the array 12 of fiber combs 17.

As shown in FIGS. 3A, and 3B, a pneumatic cylinder 20 includes a piston (not visible in the view shown) disposed within the cylinder and connected to or otherwise integral with one end of a vertically translatable piston rod 23. The opposite end of the piston rod 23 is pivotally attached to the front fiber comb 21. The free end of the piston rod 23 is pivotally connected to an elongated slotted opening 25 that is formed in the front fiber comb 21 and elongates in the direction of the length dimension of the first comb 21. A control unit controls the provision of pressurized air to the pneumatic cylinder 20. The control unit is generally designated in FIG. 1 by the number 24 and is described more fully below. The cylinder 20 is disposed so that operation of the pneumatic cylinder results in a vertical extension or retraction of the piston rod 23. The full extension of the piston rod 23 from the pneumatic cylinder 20 places the front comb 21 in the position shown in FIG. 3A for example. In this configuration, the front comb 21 is aligned with the remaining combs, including the second comb 22, of the array 12 of fiber combs 17. When the control unit 24 operates the pneumatic cylinder 20 to retract the piston rod 23 into the cylinder 20 as shown in FIG. 3B for example, the front comb 21 pivots vertically downward and drops below the height at which the remaining combs 17 are maintained in the array 12 of fiber combs 17. The pivotal connection of the free end of the piston 23 moves along the slotted opening 25 in the front fiber comb 21 in order to accommodate the pivotal motion of the front fiber comb 21.

In an alternative embodiment that is not separately illustrated, each of the opposite ends of the first fiber comb 21 can be mounted on a vertically extending track. The opposed tracks enable the first fiber comb 21 to be slidably raised and lowered to and from, respectively, the height of the other fiber combs 17 in the array 12, including the second fiber comb 22. In addition to these sliding tracks, the particular mechanism for raising and lowering the first fiber comb 21 can include a pinion gear on the end of the rotatable shaft of an electric motor. A rack gear also can be provided and connected to one of the ends of the first fiber comb 21. The pinion gear engages the rack gear so that rotation of the pinion gear powered by the motor causes the raising or lowering (depending on the direction of the rotation of the pinion gear) of the rack gear and the first comb 21 attached to the rack gear. The motor is controlled by a control unit, which is generally designated in FIG. 1 by the number 24 and described more fully below.

In accordance with the present invention, the apparatus for aligning one end of a fiber sample before testing includes a sample collection device. As embodied herein and shown schematically in FIG. 1 for example, one embodiment of a sample collection device can include a gripper comb 26. The gripper comb 26 has at least two jaws that are disposed in opposition to each other. The jaws are configured to selectively move toward and away from each other to selectively close and open, respectively. Additional mechanical details of a gripper comb 26 suited for use in the present invention are described in U.S. Pat. No. 6,085,584, which is hereby incorporated herein by this reference. Other types of gripper combs can be used. For example, the gripper jaws can be mounted on gears that are powered by an electric motor that rotates the gears in one direction to open the jaws and in the opposite direction so that the jaws come together to close with the free edges of the jaws touching each other. Alternatively, the jaws of the gripper comb 26 can be powered hydraulically or pneumatically. The collection device is connected to and activated by a preprogrammed control unit, which desirably is the same central unit 24 that controls the raising and lowering of the first comb 21.

In accordance with the present invention, the apparatus for aligning one end of a fiber sample before testing includes at least a first drive unit that is configured and disposed to carry the sample collection device and to translate the sample collection device toward and away from the first fiber comb of the array of fiber combs. As embodied herein and shown in FIG. 1 for example, a first drive unit 28 can include a first carriage formed as a plate 29 that is connected to and supports the gripper comb 26 mounted on the upper surface of the plate 29. The plate 29 of the drive unit 28 is likewise connected to a rotatable screw 30 that is rotatably powered by an electric motor 31, which is selectively activated by a preprogrammed control unit 24.

As embodied herein, the control unit 24 desirably includes a controller such as a microprocessor. Control unit 24 desirably is preprogrammed to automatically control the individual components of the various embodiments of the apparatus of the present invention to carry out the processing steps of the method of the present invention in its various embodiments. Some of the components may be hydraulically or pneumatically actuated and thus the control unit 24 would include electrically actuatable valves to control the flow of the powering fluid, be it air or an incompressible fluid such as hydraulic fluid for example. Other components of the apparatus of the present invention include electrically powered motors and switches that are electrically or electronically connected to the controller to receive control signals from the microprocessor of the control unit 24. Additionally, various components of the apparatus of the present invention include sensors and transducers that are electrically or electronically connected to the controller of the control unit 24. Such sensors and transducers carry signals to the control unit to provide the control unit 24 with information concerning the status of various components of the apparatus of the various embodiments of the present invention. Control unit 24 is preprogrammed to use the information provided by the sensors and transducers in order to determine the control signals that are returned to various components of the apparatus of the present invention. Note that the various connections between the control unit 24 and the other components shown in FIG. 1 have been omitted in order to avoid overly cluttering the drawing.

The control unit 24 determines the direction in which the drive motor 31 will rotate and the distance that the linear drive unit 28 will translate the gripper comb 26. The screw motor 31 of the first drive unit 28 turns the screw 30 that is threaded through the first carriage 29 that is slidably mounted along a first linear track that is disposed along a direction pointing directly toward and away from the array 12 of fiber combs. This direction is indicated by the line designated by the numeral 32 in FIGS. 4A-2 and 4C-2 for example. As the screw 30 is rotated in one direction, the plate 29 moves toward the array 12 of fiber combs as indicated by the arrow designated by the numeral 33 in FIGS. 4A-1, 4A-2, 4A-n and 5A for example. As the motor 31 drives the screw 30 in the opposite direction, the plate 29 and gripper comb 26 mounted thereon moves away from the array 12 of fiber combs 17 as indicated by the arrow designated by the numeral 34 in FIGS. 4C-1, 4C-2, 4C-n and 5C for example. In this way, the first drive unit 28 is configured to translate the gripper comb 26 selectively toward and away from the array 12 of fiber combs 17 by pre-selected distances.

In accordance with the present invention, the apparatus for aligning one end of a fiber sample, includes a suction device that is configured and disposed to vacuum fibers from the sample collection device. As embodied herein and shown in FIG. 1 for example, a hollow tube 36 is connected to a vacuum 37 that is driven by an electric motor, which is controlled by the control unit 24. The control unit 24 activates the motor to operate the vacuum 37, which sucks the fibers from the open jaws of the gripper comb 26. The control unit 24 is preprogrammed to determine when the first drive unit 28 has translated the gripper comb 26 to a location sufficiently distant from the array 12 of fiber combs 17 so that operation of the vacuum 37 will not vacuum fibers from the array 12 of fiber combs 17 at the same time as fibers are being vacuumed from the jaws of the gripper comb 26. Once the control unit 24 determines that the desired spatial distance exists between the end of the suction intake of the vacuum, which is disposed adjacent the jaws of the gripper comb 26, and the array 12 of fiber combs, then the control unit 24 opens the jaws of the gripper comb 26 and activates the vacuum 37. The released fibers travel through the suction intake and are carried by a hollow tube 36 to a waste chamber 38 that is desirably carried beneath a platform 13 on which the array 12 of fiber combs, the first drive unit 28 and the gripper comb 26 are carried, supported and/or connected.

In accordance with the present invention, the apparatus for aligning one end of a fiber sample includes a detection device. The detection device determines whether the end-aligned condition of the fibers remaining atop the array 12 of fiber combs 17 has been attained. As embodied herein and shown schematically in FIG. 4E-n for example, the detection device includes a sensor 40 that is disposed between the first comb 21 and the gripper comb 26.

In particular, in the embodiment that is schematically shown in FIG. 4E-n for example, the sensor 40 is a light sensor, and the detection device includes a light source 41 that is disposed on one sidewall 15 of the frame of the array 12 of fiber combs. The light sensor 40 is disposed on the opposite sidewall 16 of the frame and aligned with the light source 41 so as to intercept the light beam emitted from the light source. The light source 41 is connected to the control unit 24, which operates the light source to generate a light beam between the source 41 and the sensor 40. The light source 41 is aimed so as to project the light beam in a straight line along the length of the first comb 21 at a position just in front of and parallel to the first comb and at a height where the free ends 39 of the fibers carried by the first comb 21 would be expected to intercept the light beam. The light beam desirably is a focused beam of coherent light such as would be produced by a light source 41 that is a laser The light sensor 40 is connected to the control unit 24 and generates signals proportional to the degree of attenuation of the light beam and transmits these signals to the control unit 24. At a predetermined degree of attenuation of the light beam, the signal that is generated by the light sensor 40 is interpreted by the control unit 24 as indicating that the free ends 39 of the fibers supported by the first comb 21 are in an end-aligned condition. The detection device is accordingly configured to determine whether the end-aligned condition of the fibers remaining atop the array 12 of fiber combs has been produced.

Figure 2A:
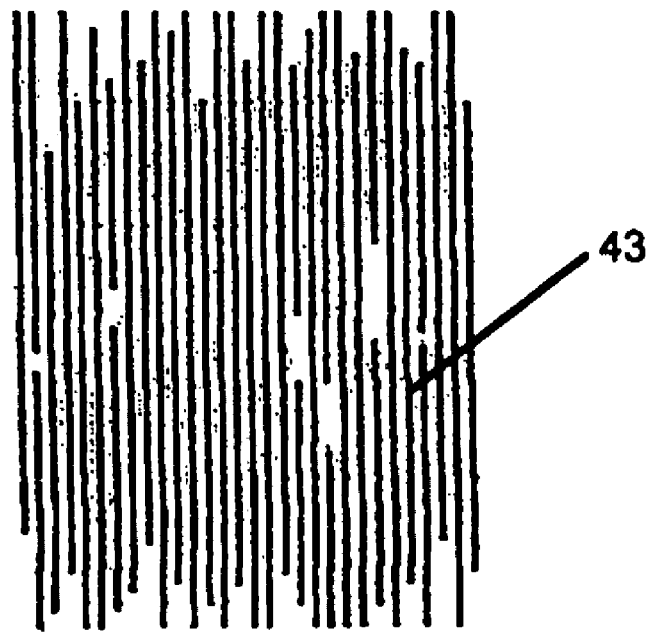
FIG. 2A shows a top plan view of a fiber sample in a state in which neither end of the sample has been end-aligned.
Figures 1, 4A:
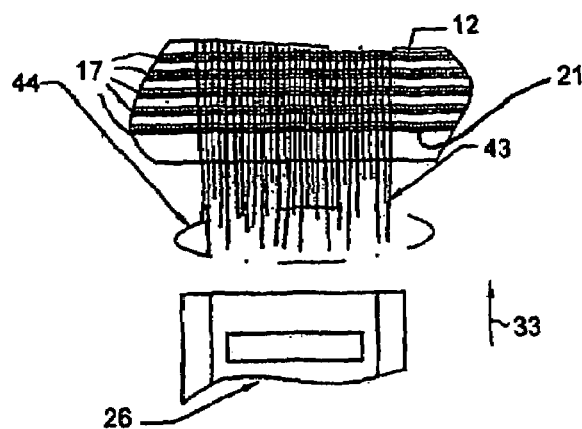

Operation of an embodiment of the apparatus and method of the present invention now will be described. In one embodiment, a non-end-aligned fiber sample 43 such as shown schematically in FIG. 2A is selected for testing. The non-end-aligned fiber sample 43 is constituted as an assembly of elongated fibers disposed side-by-side and arranged with the lengths of the individual fibers extending in a direction that is generally parallel to each other. The non-end-aligned fiber assembly 43 is manually placed on the needles of the fiber combs in the array 12 of fiber combs 17. As schematically shown in FIG. 4A-1, the fibers in the fiber assembly 43 are oriented with their lengths disposed in a direction that is normal to the length direction of the first fiber comb 21. Thus, the fiber assembly 43 is oriented with the direction of elongation of the fibers in the fiber assembly 43 is perpendicular to the direction of the lengths of the fiber combs 17.

After placement of the fiber assembly 43 on the array 12 of needles, the apparatus looks similar to that shown schematically in FIG. 4A-1 with the array 12 of combs disposed directly beneath the fiber assembly 43 ready for starting the preparation processing that results in an end-aligned sample. At this stage, the fibers are arranged in a random fashion as shown schematically in FIG. 2A. Different lengths of the individual fibers protrude beyond the front edge of the array 12, this front edge being defined by the exposed side of the first comb 21 in the needle array 12.

Figure 2B:
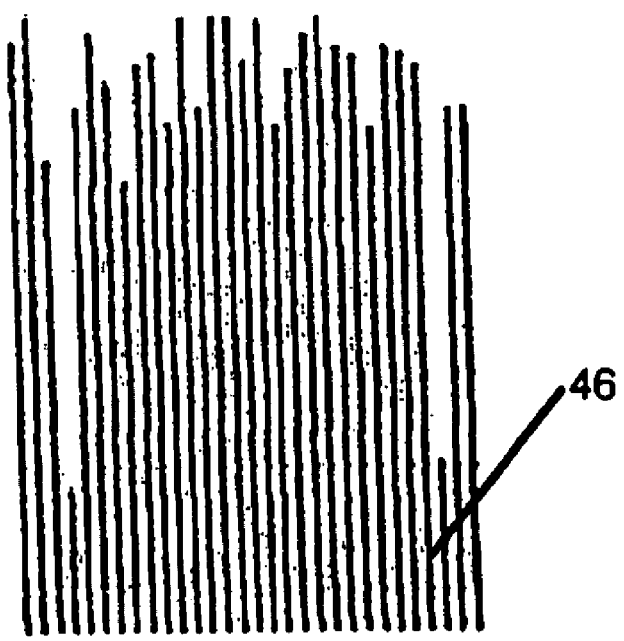
FIG. 2B shows a top plan view of a fiber sample in a state in which one end of the sample has been end-aligned in accordance with one aspect of the present invention.

The sample preparation process is now commenced wherein the objective is to produce an end-aligned sample 46 having its fibers aligned at one end as shown in FIG. 2B. This is achieved by a repetitive action of the gripper comb 26 on the fiber assembly 43 at the end protruding from the front edge of the array 12 of needles 18. Briefly, the gripper comb 26 moves to the fiber assembly 43, closes on fibers that protrude into the jaws, backs away from the fiber assembly 43 with some of the fibers, discards the fibers that have been acquired, senses the condition of the ends of the fibers that remain part of the fiber assembly 43, and then returns to the fiber assembly 43 for more of the fibers in a number of successive operations until only end-aligned fibers remain atop the array 12 of fiber combs 17. Note that while these processing steps occur in succession, the order of the discarding step and the sensing step can be reversed or can occur at the same time. Similarly, the sensing step can occur before the backing away step is completed.

A first operational sequence of the apparatus and method for aligning one end of a fiber sample is schematically represented in FIGS. 4A-1, 4B-1, 4C-1 and 4D-1. The sequence begins after the fiber sample 43 has been placed manually atop the array 12 of fiber combs 17. The jaws of the gripper comb 26 are opened. The control unit 24 is programmed to control the motor or other power device that drives the movement of the jaws of the gripper comb 26.

As schematically shown in FIG. 4A-1, the gripper comb 26 having its jaws open is moved in the direction of arrow 33 that is towards the fiber assembly 43. The open jaws of the gripper comb 26 are moved toward the fiber assembly 43 by operation of the first drive unit driven by the motor under the control of the control unit. This initial movement of the gripper comb 26 continues until the control unit determines that a predetermined linear distance from the first comb 21 of the array 12 of fiber combs has been attained. This predetermined distance is selected so that at least some of the protruding ends (indicated schematically by the oval designated by the numeral 44 in FIG. 4A-1) of the fibers in the sample will project into the jaws of the gripper comb 26. The control unit limits the approach of the gripper comb 26 to the first fiber comb 21 in the array 12 to this predetermined first distance.

Figures 1, 4B:
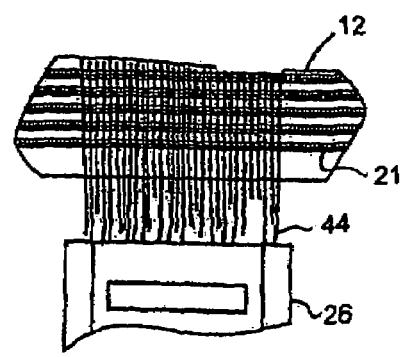

The sequence next involves closing the jaws of the gripper comb 26 to hold the fibers projecting into the jaws of the gripper comb 26. As schematically shown in FIG. 4B-1, the control unit operates the gripper comb 26 to close its jaws so as to grip the ends 44 of the fibers that project into the jaws of the gripper. Closure of the jaws of the gripper comb 26 in this manner grips the fibers between the jaws of the gripper comb 26. In one alternative embodiment, the control unit operates the motor in the direction that drives the gear to move the jaws toward each other until they meet sufficient resistance that the jaws are considered to be in a closed condition. A pressure transducer (not shown) can provide this information by generating appropriate signals that are communicated to the control unit 24.

Figures 1, 4C:
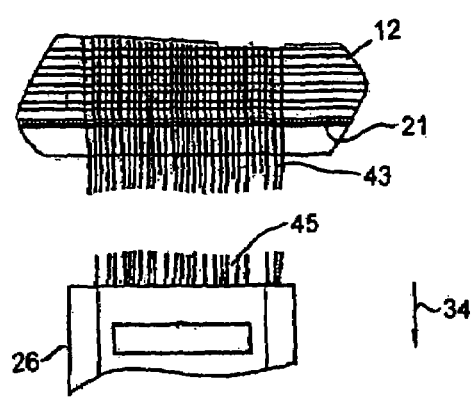

As schematically shown in FIG. 4C-1, the closed jaws of the gripper comb 26 are moved away from the fiber assembly. The control unit operates the first drive unit to retract the gripper in a linear but opposite direction 34 away from the fiber assembly 43. As the gripper comb 26 retracts, some fibers 45 are pulled from the fiber assembly 43 supported atop the array 12 of combs. In one embodiment shown schematically in FIG. 1 for example, the motor 31 under the control of the control unit 24 drives operation of the first drive unit 28. The control unit is programmed to move the gripper 26 until the gripper is disposed to a predetermined location. That location must be sufficiently distant from the first comb 21 in the array 12 of fiber combs so that suction of fibers 45 from the gripper 26 will not vacuum fibers from the fiber assembly 43 remaining on the array 12 of fiber combs 17.

The fibers that have been pulled from the fiber assembly 43 must be removed from the gripper comb 26. The control unit 24 configures the collection device 26 to release the fibers 45 that have been pulled from the fiber assembly 43 carried by the array of fiber combs. In one alternative embodiment, the control unit operates the motor in the direction that drives the gear to move the jaws away from each other until they separate a predetermined distance such that the jaws are considered to be in an opened condition. By opening the jaws of the gripper comb 26 in this manner, the fibers 45 projecting into the jaws of the gripper comb 26 are released.

Figures 1, 4D:

As schematically shown in FIG. 4D-1, the fibers that have been removed from the fiber assembly and released from the gripper 26 are discarded by being suctioned away from the gripper comb 26. In one embodiment shown in FIG. 1, the control unit 24 operates the motor that powers the vacuum 37 with the effect of suctioning away the released fibers from the jaws of the gripper comb 26. The released fibers are thus removed by suction to a waste chamber 38 via the intake of the suction hose 36 that leads to the waste chamber carried 38 in a cabinet 14 beneath the platform 13.

The process also requires determining whether the end-aligned condition of the assembly of fibers remaining atop the array of fiber combs has been produced. In the embodiment schematically shown in FIG. 4E-n, this determination can be made by scanning the edge of the fiber assembly 43 by optical methods. The edge of the fiber assembly 43 is formed by the free ends 39 of the fibers that remain part of the fiber assembly 43. These free ends 39 extend beyond the first comb 21 toward the gripper 26. The control unit 24 activates the light source 41 to project the light beam to the light sensor 40. The light sensor 40 generates signals proportional to the degree of attenuation of the light beam and transmits these signals to the control unit 24. At a predetermined degree of attenuation of the light beam, the signal that is generated by the light sensor 40 is interpreted by the control unit 24 as indicating that the free ends 39 of the fibers supported by the first comb 21 are in an end-aligned condition. However, failing to receive such a signal from the light sensor, the control unit is programmed to interpret the result as indicating that the end-aligned condition has not been achieved.

By calibrating the apparatus with different types of fiber assemblies, it is also possible to pre-set the number of times the gripper comb 26 has to act on the fiber assembly 43 in order to attain an end-aligned condition.

As noted above, the order of the suctioning step and the step of determining whether the end-aligned condition has been attained in the fibers that remain on the array 12 of fiber combs 17 can be reversed or can occur at the same time. Similarly, the step of determining whether the end-aligned condition has been attained in the fibers that remain on the array 12 of fiber combs 17 can begin to occur before the step of moving the gripper comb 26 away from the array 12 of fiber combs 17 is completed.

Figures 2, 4A:
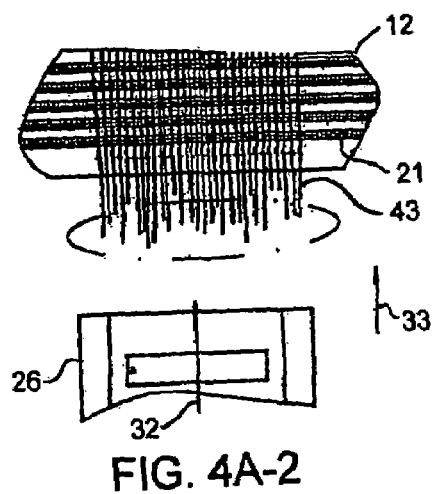
Figures 2, 4B:
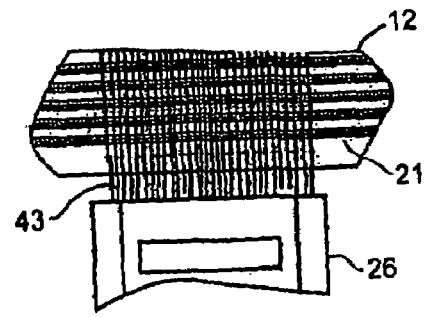
Figures 2, 4C:
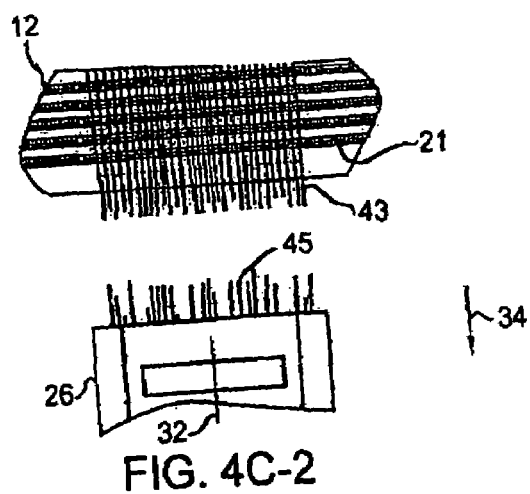
Figures 2, 4D:
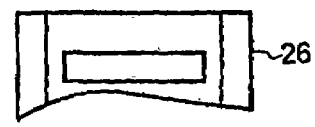

Upon determining the absence of the end-aligned condition, the control unit 24 is programmed to restart the entire sequence whereby the gripper 26 makes a closer approach to the front fiber comb 21 than in the immediately preceding trip. This second operation of the sequence is schematically represented by FIGS. 4A-2, 4B-2, 4C-2 and 4D-2. As schematically shown in FIG. 4A-2, the control unit thus activates the motor to operate the first drive unit in the direction 33 that moves the open jaws of the gripper comb 26 toward the fiber assembly 43. As schematically shown in FIG. 4B-2, once the gripper comb 26 is disposed at a second distance from the front fiber comb 21 that is less than the distance that was attained in the immediately preceding trip, at least some of the remaining fibers of the fiber assembly 43 project into the jaws of the gripper comb 26. Once the gripper comb 26 is disposed at this second distance, the control unit operates the jaws of the gripper comb 26 to close and grip onto the fibers that project into the jaws. As schematically shown in FIG. 4C-2, the closed jaws of the gripper comb 26 are moved in a direction 34 away from the fiber assembly 43. As the gripper comb 26 retracts, some fibers 45 are pulled from the fiber assembly 43 supported atop the array 12 of combs. The jaws of the gripper comb 26 are opened to release the fibers 45 that have been removed from the fiber assembly 43. As schematically shown in FIG. 4D-2, the fibers that have been removed from the fiber assembly and released from the gripper have been suctioned away from the gripper comb 26. As schematically shown in FIG. 4E-n, the control unit 24 then operates the detection device to determine whether the end-aligned condition of the fiber assembly 4 has been attained.

If the end-aligned condition of the fiber assembly has not been attained, then the sequence is repeated until with the nth repetition, the end-aligned condition has been attained. This successive repetition of the sequence of operations of the apparatus and method for preparing an end-aligned fiber sample for "n" times is schematically represented by FIGS. 4A-n, 4B-n, 4C-n, 4D-n and 4E-n.

Once it is determined that the end-aligned condition of the fiber assembly supported atop the array of fiber combs has been attained, then the end-aligned sample is ready for collection by the gripper comb 26. As embodied herein and schematically shown in FIGS. 3B and 5A for example, the first fiber comb 21 in the array of fiber combs is removed to permit easier access of the jaws of the gripper comb 26 to firmly grip the end-aligned ends of the fiber sample 46. As embodied herein, the control unit 24 is preprogrammed to vertically lower the first comb 21 beneath the height of the second comb 22. Once this forward-most comb 21 in the array 12 of needles 18 is lowered, the control unit can move the open jaws of gripper 26 to assume the position shown in FIG. 5B. As shown schematically in FIG. 5B for example, then the control unit can close the jaws of the gripper 26 onto the end aligned fiber sample 46. At this stage, the gripper comb 26 grips the end-aligned edge of the end-aligned fiber tuft 46 and thus collects a sample beard for testing.

Figure 5D:
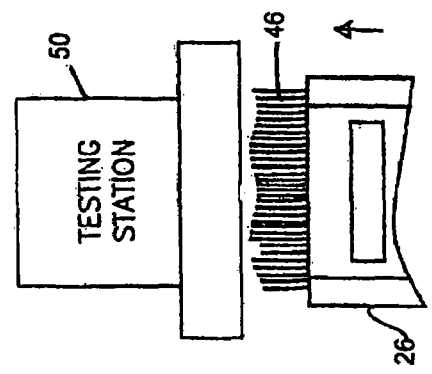
FIG. 5D schematically shows a top plan view of a portion of a component of an embodiment of the present invention, shown in FIG. 5C in relation to a testing station.
Figure 5A:
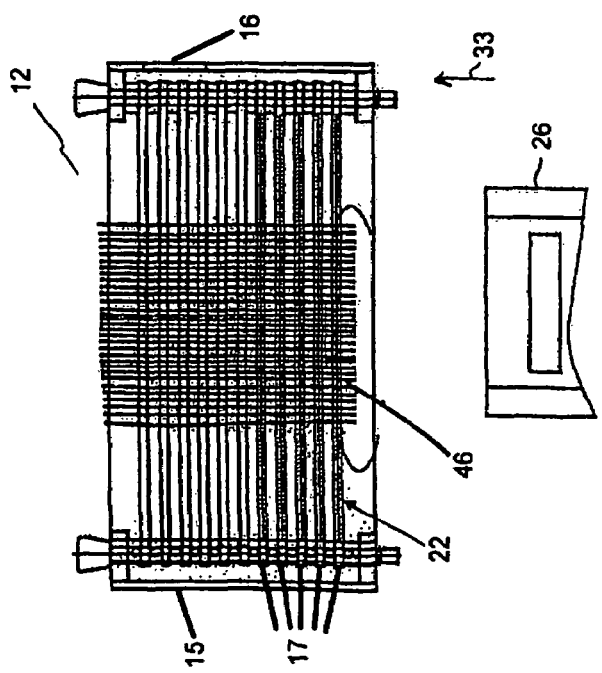
FIG. 5A schematically shows a top plan view of portions of components of an embodiment of the present invention.
Figure 5C:
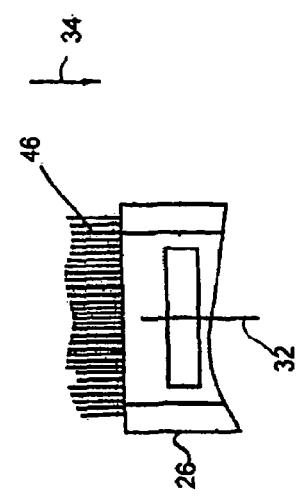
FIG. 5C schematically shows a top plan view of portions of components of an embodiment of the present invention shown in FIG. 5B.

Once the gripper 26 collects the end-aligned sample 46 from the needle array, the control unit can move the gripper 26 away from the array 12 of fiber combs as shown schematically in FIG. 5C. As shown schematically in FIG. 1 for example, after this sample collection, the gripper comb 26 moves the end-aligned fiber sample 46 towards a first testing station 50. The movement of the gripper comb 26 towards the testing station 50 proceeds in a direction that is perpendicular to the movement towards the needle array 12 but can be in the same plane. As shown schematically in FIG. 1 for example, this movement to the first testing station 50 can be accomplished desirably by a second drive unit 48 that is configured and disposed to move linearly in a direction that is perpendicular to the direction along which the first drive unit 28 moves. The second drive unit 48 can be connected to the first drive unit 28. As shown schematically in FIG. 1 for example, the control unit 24 activates the second drive unit 48 so that the first drive unit 28 and the gripper comb 26 move linearly towards the testing station 50 until the second drive unit 48 takes up the position of the dashed line outline of the second drive unit 48. The gripper comb 26 reaches the testing station 50 when the second drive unit takes up the position of the dashed line outline of the second carriage 48 shown in FIG. 1.

The movement of the gripper comb 26 from the fiber comb array 12 to the testing station 50 could be effected in many ways other than the one mentioned, depending on the construction and depending on location of the testing station 50 relative to the needle array 12. It is possible to have a movable testing station 50 wherein after the sample is collected and oriented towards the testing station 50, the testing station 50 moves to a position near the sample in a way convenient to start the testing process. Alternatively, as described hereafter in connection with multi-gripper embodiments, a pick and place mechanism and a guideway can be employed to transfer to the first testing station 50, the first carriage 29 with or without the first drive unit 28.

When the gripper comb 26 reaches the testing station 50, as shown schematically in FIG. 5D for example, then the control unit can present the end-aligned sample 46 for testing. The operation of the apparatus for aligning one end of a fiber sample before testing, can be part of a larger overall apparatus and/or method of testing a fiber sample taken from a supply of fibers. In the instance of the use of the present invention, the fiber sample to be tested in such a larger overall method desirably will have an end-aligned condition before certain aspects of the testing are performed.

Figure 8:
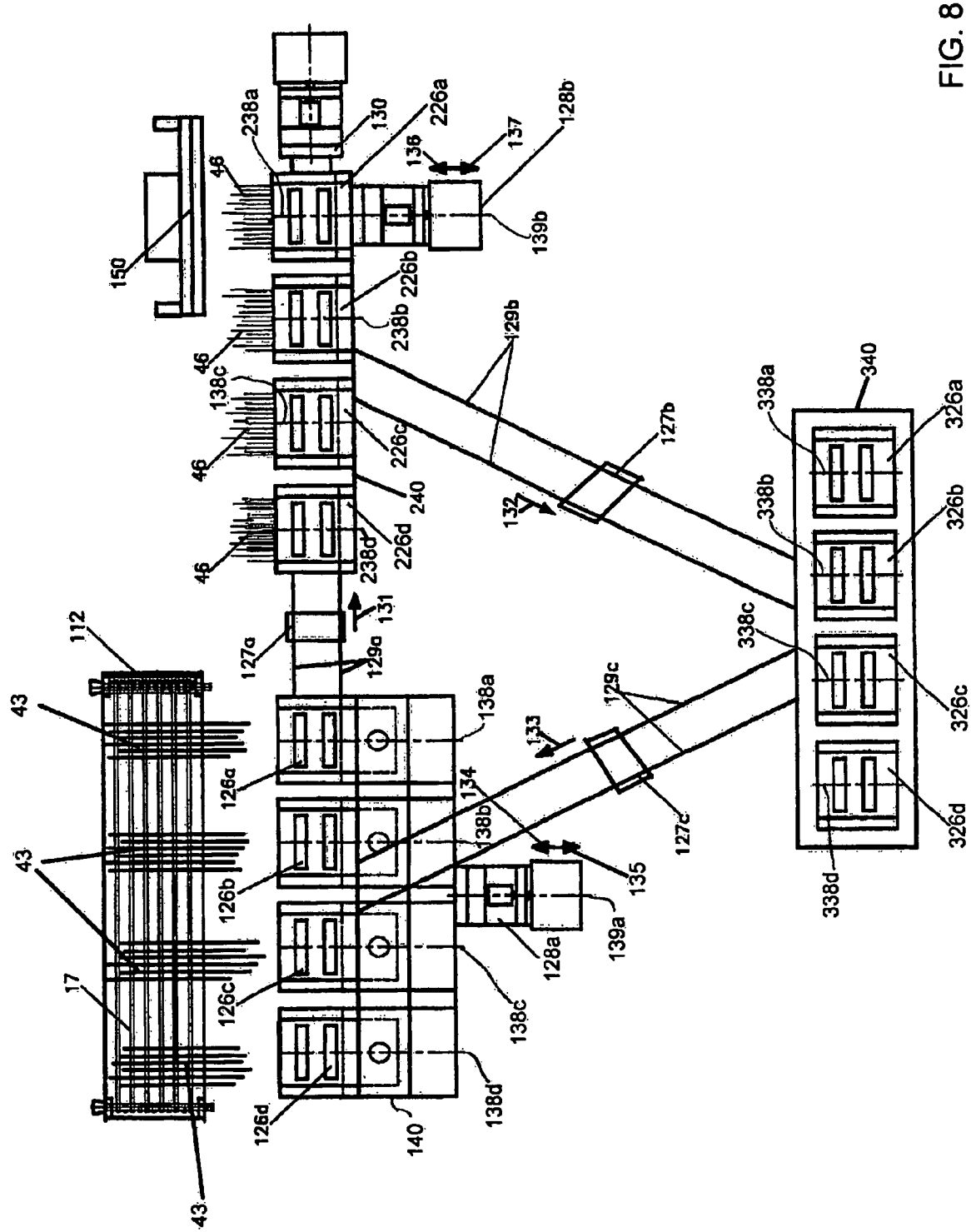
FIG. 8 shows a top plan view of another embodiment of the apparatus of the present invention having multiple gripper combs.

If the testing station 50 is one that is configured for measurement of the length characteristics, then the testing station 50 can comprise an optical device such as an LED array source and array receiver located on either side of a slotted opening 51 as schematically shown in FIGS. 1 and 8. Such a device can be used to determine the proportion of short fibers in the sample 46. As shown schematically in FIG. 1 for example, when the testing station 50 and the end-aligned sample are ready for testing the length of the fibers, the sample beard is gradually moved inside the slotted opening 51 of the testing module 50 with the free ends moving in first. The control unit 24 can effect such movement by activating the first drive unit 28 for example. When the sample moves inside the slotted opening 51, the light beam from the LED source 52 is interrupted resulting in a variation in the amount of light received by the receiver 53. The extreme free end of the sample beard contains only the longest fiber held by the gripper 26. As the beard is successively scanned with each incremental displacement deeper into the slotted opening 51, the number of fibers interrupting the light gradually increases. The interruption thus gradually increases to reach a maximum at a point close to the gripping point. A suction device 49 is provided for removing the tested fiber beard, if desired, and transporting the thus discarded fibers to the waste chamber 38 via a hollow waste tube 35.

Figure 6:
FIG. 6 is a diagram showing the output of a detector.
Figure 7:
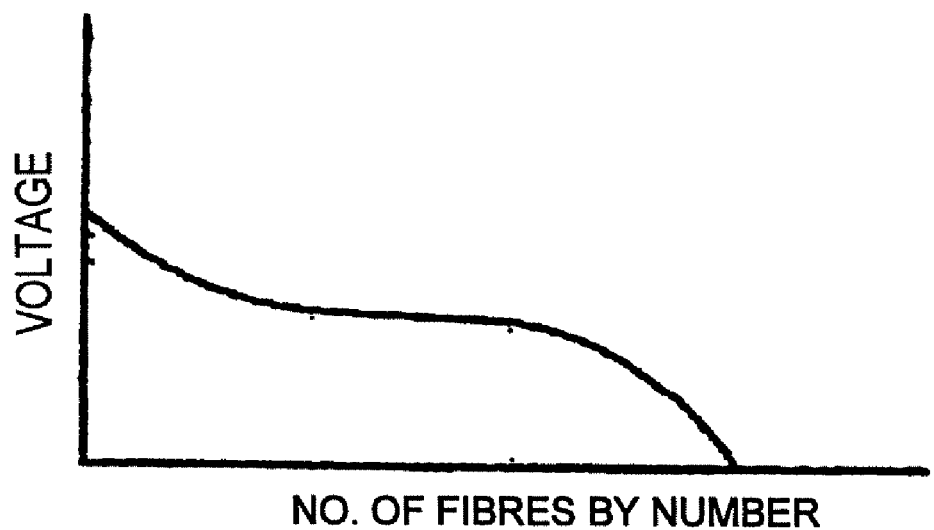
FIG. 7 is a diagram showing the output of a detector.

The signal obtained with the above method is similar to that shown in FIG. 6. For ease of explanation, it was mentioned in the earlier paragraph that the amount of interruption is in proportion to the number of fibers. This is possible only when all the fibers being scanned are of uniform diameter. In a practical situation, all fibers do not have the same diameter, and therefore the amount of interruption of light is proportional to only the optical mass of fibers at any given instant. The diagram thus generated and shown in FIG. 6 is therefore proportional to the "length by weight." In the textile industry, in addition to the "length by weight," "length by number" is also widely used. Conversion from the length-by-weight to length-by-number (FIG. 7) is achieved easily if a constant diameter or linear density is assumed.

In an alternative embodiment shown schematically in FIG. 4E-n for example, it is also conceivable to have an instrument where the comb is initially placed in such a way that the gripper 26 is closest to the light source 41 at the initial point. For example, until the end-aligned fiber sample 46 is produced, the optical detection device 40 that is used by the control unit 24 to sense when the ends of the fibers have attained the end-aligned condition can be used to perform a length measurement for the fibers in the end-aligned sample. With such a method, the gripper comb 26 is moved in such a way that the gripping point moves successively farther and farther a short distance from the light path. In such a situation, the amount of interruption in the light (optical mass) gradually decreases from start to finish of the gripper's movement. The control unit 24 can accomplish this process by activating the first drive unit 28 in successive short movements away from the array 12 of fiber combs. After each short movement of a predetermined distance from the array 12 of fiber combs 17, the control unit 24 activates the light source 41 and receives a signal from the light detector 40. As explained above, the optical sensor is disposed at a set distance relative to the front of the array 12 of fiber combs 17. The control unit 24 is programmed to interpret this signal as indicative of the number of fibers that interrupt and attenuate the light beam when the gripper comb 26 is disposed at a known distance from the array 12 of fiber combs. This number of fibers must have a length that is at least equal to that separation distance.

A desirable alternative embodiment of the mechanism for preparation and transport of the end-aligned fiber sample includes an apparatus for aligning at substantially the same time, one end of each of at least two fiber samples before testing. In this multi-sample apparatus, each of the received samples includes an assembly of elongated fibers disposed side-by-side and arranged with the lengths of the individual fibers extending in a direction that is generally parallel to each other. Such an apparatus is illustrated schematically in FIG. 8 and is configured to align at substantially the same time, one end of each of four fiber samples 43 before processing and/or testing. As will become apparent upon reading the description below, the number of fiber samples 43 that can be end-aligned at substantially the same time in the multi-sample, end-aligning apparatus can be varied by changing the sizes of various components of the apparatus.

As embodied herein and shown schematically in FIG. 8 for example, the multi-sample, end-aligning apparatus includes an extended needle array 112 that is long enough to support a number of discrete, non-end-aligned samples 43 (each sample 43 as shown schematically in FIG. 2A for example) arranged side-by-side. Extended needle array 112 is configured substantially as fiber comb array 12 shown in FIGS. 1, 3A, 3B, 5A and 5B for example, except that extended needle array 112 is longer across the front than fiber comb array 12. The increased length of extended needle array 112 serves to accommodate the simultaneous preparation of multiple fiber samples 43 into the desired end-aligned condition.

As embodied herein and shown schematically in FIGS. 8-14 for example, the multi-sample, end-aligning apparatus includes a multi-stage gripper comb 140 that has at least a first gripper comb 126a and a second gripper comb 126b disposed adjacent the first gripper comb 126a. The individual gripper combs 126a, 126b are connected together to move in unison. In the embodiment shown, the multi-stage gripper comb 140 includes four individual gripper combs 126a, 126b, 126c, 126d arranged side-by-side. A third gripper comb 126c is disposed adjacent the second gripper comb 126b, and a fourth gripper comb 126d is disposed adjacent the third gripper comb 126c. All four gripper combs 126a, 126b, 126c and 126d are connected together to move in unison as a multi-stage gripper comb 140. Each individual gripper comb 126a, 126b, 126c, 126d operates substantially as gripper comb 26 described above and shown in FIG. 1 for example.

Figure 9:
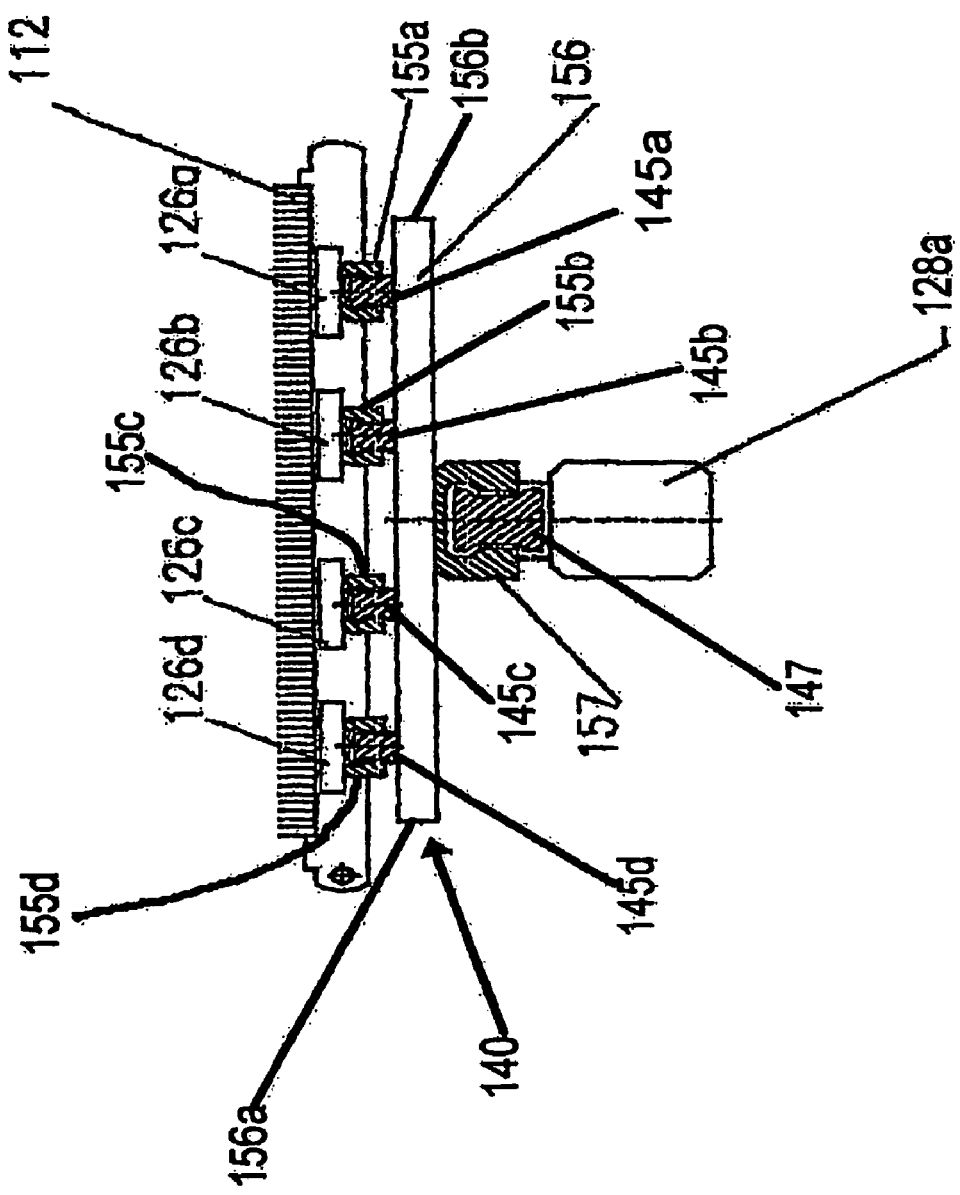
FIG. 9 schematically presents a front plan view of components (some shown in cross-section) of the embodiment of the apparatus of the present invention shown in FIGS. 8, 10 & 11.

As schematically shown in FIG. 9 for example, each individual gripper comb 126a, 126b, 126c, 126d is fitted with a respective base 155a, 155b, 155c, 155d in is the form of a sleeve that is slidably mounted to one portion of a separate respective pedestal 145a, 145b, 145c, 145d. The interior configuration of each base 155 and the complementarily-shaped one portion of each respective pedestal 145 together form a sliding dove-tail arrangement that permits relative sliding movement in the directions indicated by the arrows 134 and 135 in FIG. 8. An opposite portion of each pedestal 145 is fixed to the upper side of a first carriage 156 that defines a platform for supporting and carrying a plurality of individual gripper combs 126. Thus, a multi-stage gripper comb 140 comprises the individual gripper combs 126a, 126b, 126c and 126d, their respective bases 155a, 155b, 155c, 155d and pedestals 145a, 145b, 145c, 145d and the first carriage 156.

Moreover, the base 155 and corresponding pedestal 145 of each individual gripper comb 126a, 126b, 126c and 126d is provided with a mechanism (not shown) that selectively locks and unlocks the gripper comb 126 against sliding movement of the base 155 relative to its respective pedestal 145 in the directions indicated by the arrows 134 and 135 in FIG. 8. The selective locking and unlocking of each base 155 to its respective pedestal 145 is desirably under the control of the control unit 24.

As schematically shown in FIG. 9 for example, the underside of the first carriage 156 is selectively attachable and detachable to a support 157. The support 157 and the first carriage 156 are provided with a mechanism (not shown) that selectively locks and unlocks the support 157 to the first carriage 156. The selective locking and unlocking of the support 157 to the first carriage 156 is desirably under the control of the control unit 24.

As schematically shown in FIG. 9, support 157 is desirably configured in the form of a sleeve that is slidably mounted to one portion of a pedestal 147 that forms part of a first drive unit 128a that is operated under the control of the control unit 24. The interior configuration of each support 157 and the complementarily-shaped one portion of the pedestal 147 together form a sliding dove-tail arrangement that permits relative sliding movement in the directions indicated by the arrows 134 and 135 in FIG. 8. The first drive unit 128a functions under the control of the control unit 24 to power the movement of the multi-stage gripper comb 140 in the directions indicated by the arrows 134 and 135 in FIG. 8 in substantially the same manner as the coordinated operation of control unit 24 with first carriage 28 and motor 31 shown in FIG. 1.

As embodied herein and shown schematically in FIG. 8 for example, each of the individual gripper combs 126a, 126b, 126c, 126d in multi-stage gripper comb 140 is aligned in front of its own respective individual non-end-aligned sample 43. The individual gripper combs 126a, 126b, 126c, 126d are aligned side-by-side in a row on first carriage 156. In this way, multi-stage gripper comb 140 can be made to approach and recede, selectively, under control of the control unit 24, to and from the extended needle array 112. The multi-stage gripper comb 140 is engaged by a first drive 128a that is configured to move the entire row of gripper combs 126a, 126b, 126c, 126d simultaneously with respect to the extended needle array 112 under the control of the control unit 24. The first carriage 156 carries the entire row of gripper combs 126a, 126b, 126c, 126d in the linear directions of the arrows designated by the numerals 134 and 135 in FIG. 8. While there is a row of four gripper combs 126a, 126b, 126c, 126d aligned side-by-side in the embodiment shown in FIG. 8, that number can be varied to accommodate extended needle arrays 112 of commensurate dimensions.

In this way, these individual gripper combs 126a, 126b, 126c, 126d are moved simultaneously by the first drive unit 128a and first carriage 156 with respect to the needle array 112 for simultaneous preparation of each of the end-aligned fiber samples 46 in the same manner described in detail for the single gripper comb 26 shown in FIG. 1. However, the detection of four end-aligned fiber samples 46 will not be accomplished until each of the non-end-aligned fiber samples 43 (all four in the embodiment shown in FIG. 8) has attained the desired end-aligned condition that is shown for the end-aligned samples 46 in FIGS. 2B and 10 for example.

Figure 10:
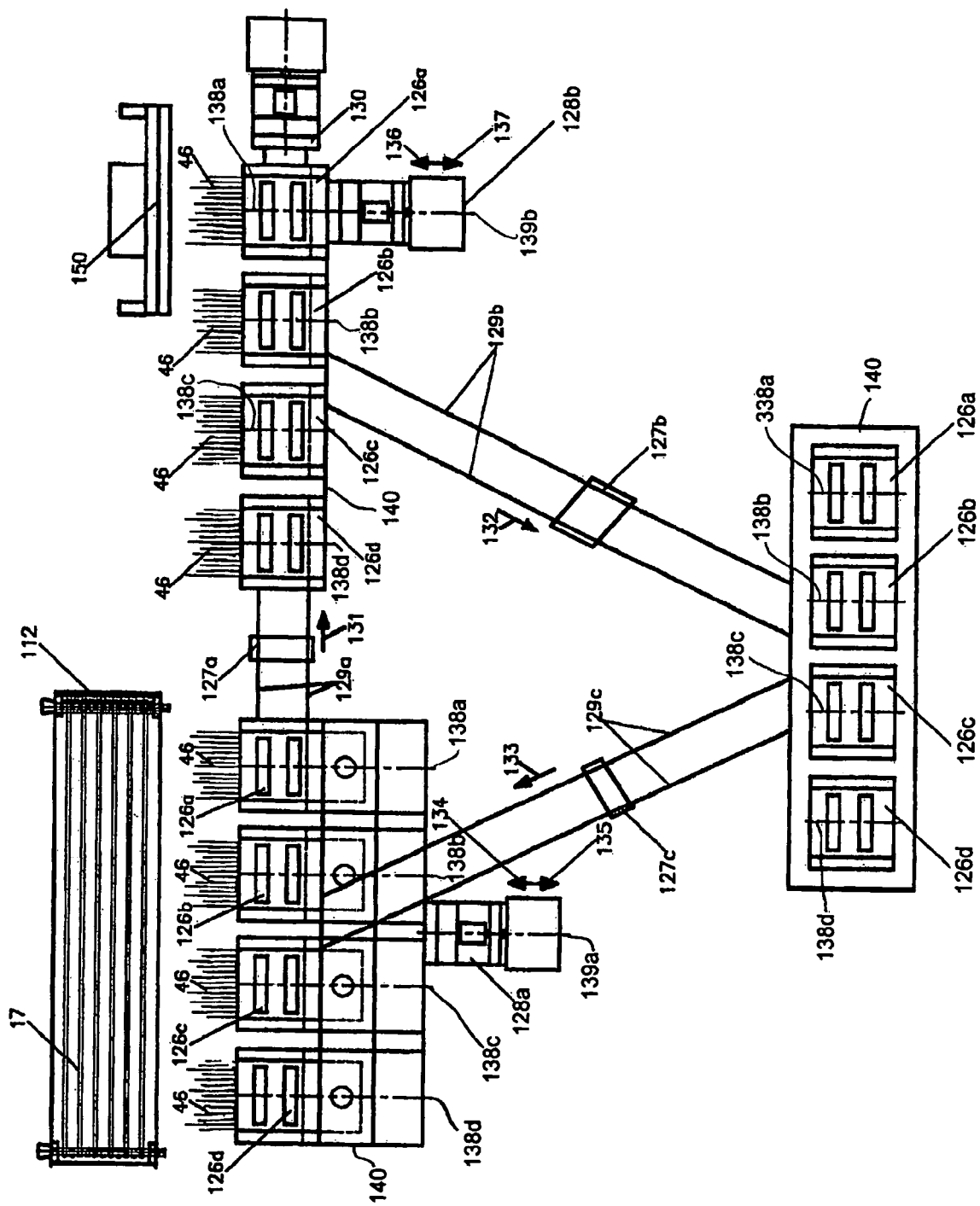
FIG. 10 shows a top plan view of the embodiment of the apparatus of the present invention having multiple gripper combs shown in FIG. 8.

After the preparation of the end-aligned samples 46 is complete, then the multi-stage gripper comb 140 simultaneously removes all of the end-aligned samples 46 from the needle array 112 and retracts from array 112 as shown schematically in FIG. 10 for example. Each individual gripper comb 126a, 126b, 126c, 126d will grip the end-aligned edges of its respective end-aligned sample 46, and then the control unit 24 will cause the first drive unit 128a to move the first carriage 156 in the direction of arrow 135 in FIG. 10. Then the multi-stage gripper comb 140 must be acquired by the holder of a first pick and place mechanism.

Figure 11:
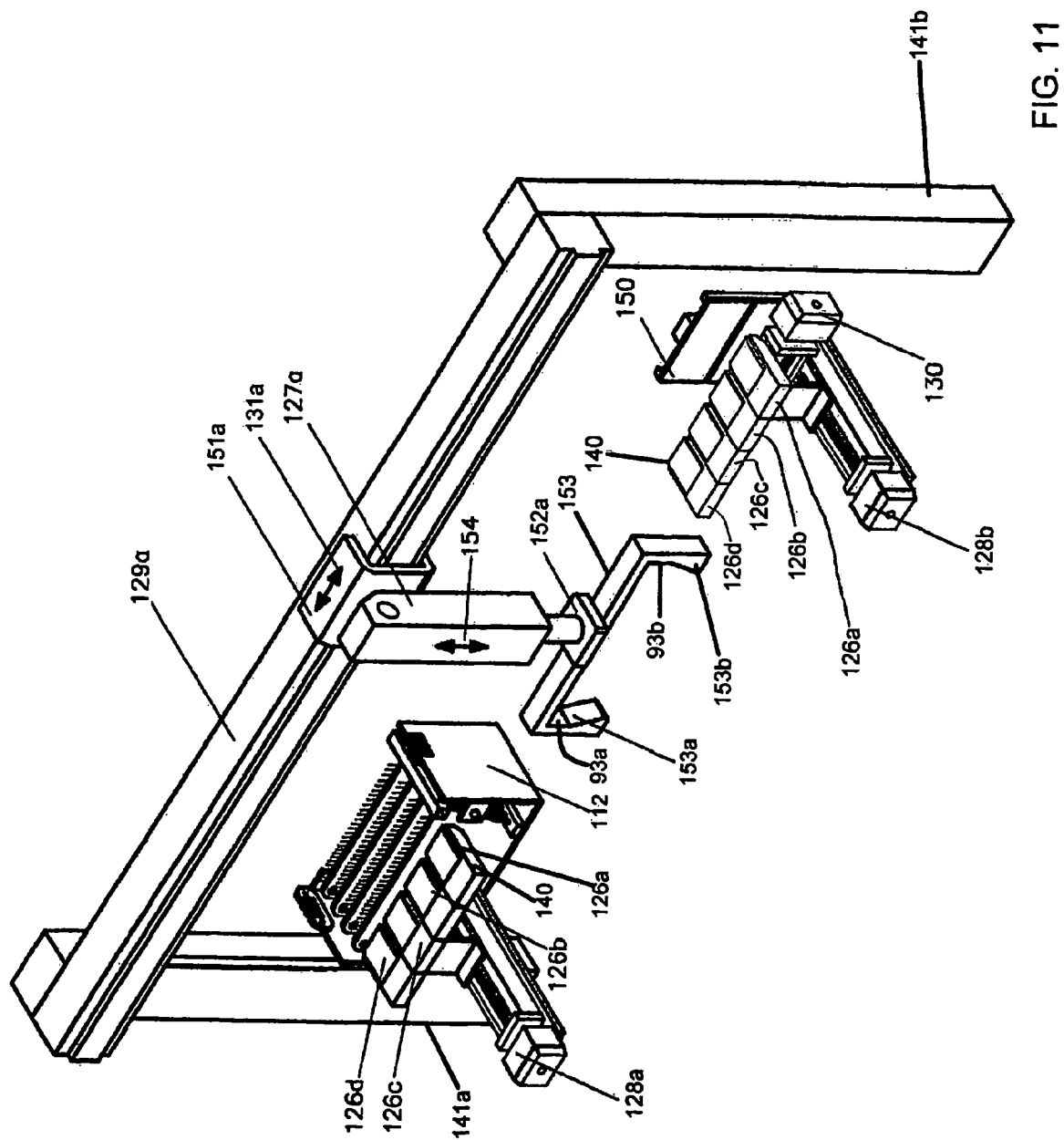
FIG. 11 schematically presents an elevated perspective view of components of the embodiment of the apparatus of the present invention shown in FIGS. 8 & 10.
Figure 15:
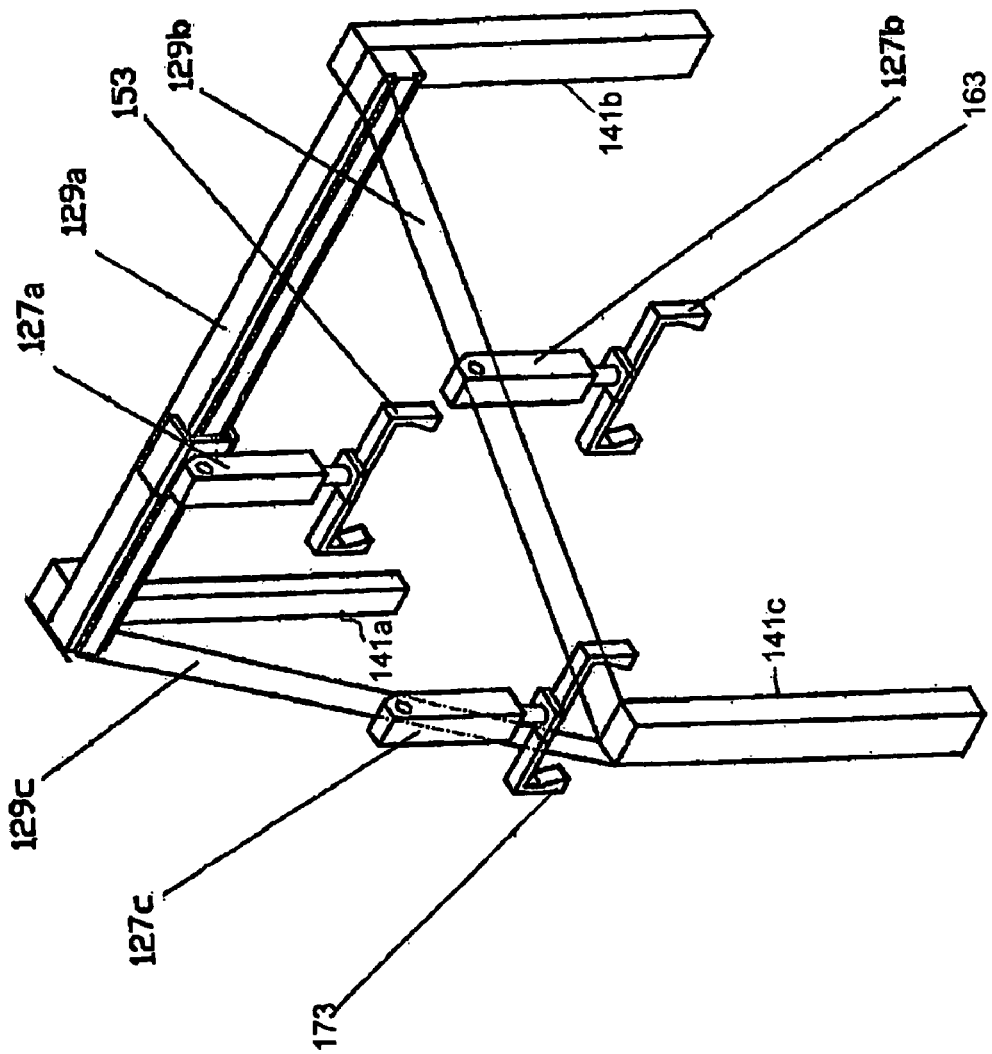
FIG. 15 schematically presents an elevated perspective view of components of the embodiment of the apparatus of the present invention shown in FIGS. 10, 11 & 12.

As shown schematically in FIGS. 8, 10, 11 and 15 for example, a first guideway 129a is configured and disposed to map the desired movement of the multi-stage gripper comb 140 between the extended needle array 112 and a first testing unit 150. As shown in FIGS. 11 and 15 for example, first guideway 129a can be elevated above first carriage 128a and extended needle array 112 by being connected on each opposite end to the elevated end of a vertically extending stanchion 141a, 141b. Extended needle array 112 and a first testing station 150 are disposed between first stanchion 141a and second stanchion 141b. First stanchion 141a is disposed nearer to extended needle array 112. Second stanchion 141b is disposed nearer to first testing station 150.

As shown schematically in FIG. 11 for example, a first trolley 151a engages and is carried by the first guideway 129a. The first trolley 151a is mobile with respect to the first guideway 129a and desirably is pneumatically powered for movement back and forth in the directions indicated by the arrows designated 131a in FIG. 11. Movement of the first trolley 151a desirably is under the control of the control unit 24.

As embodied herein and shown schematically in FIGS. 10 and 11 for example, a suitable first pick and place mechanism 127a can be provided to be carried along a suitably disposed and configured first guideway 129a. As embodied herein and shown schematically in FIG. 11 for example, one end of first pick and place mechanism 127a is connected to the first trolley 151. The opposite end of first pick and place mechanism 127a is configured as a first holder 153. First holder 153 desirably can be provided with a pair of opposed arms 153a, 153b. The distance between the free ends of the opposed arms 153a, 153b gradually increases as one moves from the arm's free end toward the end of the first pick and place mechanism 127a that is connected to the first trolley 151a. As shown in FIG. 11, the widest expanse between the opposed arms 153a, 153b of the first holder 153 is defined between respective opposed upper inwardly-facing surfaces 93a, 93b of the arms 153a, 153b.

As shown in FIG. 11, the first pick and place mechanism 127a can include a first telescoping member 152a that selectively elongates and contracts in the direction of opposed arrows 154. The telescoping action of the first pick and place mechanism 127a changes the height of the first holder 153 relative to the first guideway 129a and the extended needle array 112. Desirably, the first telescoping member 152a can be powered by a dual-action pneumatic cylinder connected to a pressurized pneumatic source via electrically actuated valves (not separately illustrated) that are operated according to the instructions of control unit 24. Suitable devices for functioning as pick and place mechanisms in accordance with the present invention can be obtained from Festo AG and Co., Esslingen, Germany.

When multi-stage gripper comb 140 has collected the multiple end-aligned fiber samples and is disposed in front of needle array 112 as shown in FIG. 10 for example, first pick and place mechanism 127a acquires multi-stage gripper comb 140 in the following manner. Control unit 24 causes first trolley 151a to move toward first stanchion 141a until the opening that is defined between the opposed arms 153a, 153b of first holder 153 is centered about the opposite ends of multi-stage gripper comb 140. Control unit 24 activates telescoping member 152a so as to adjust the vertical height of first holder 153 so that the maximum opening distance between the arms of holder 153 is precisely located at the same height as the opposite edges of multi-stage gripper comb 140. In this condition, the upper surfaces 93a, 93b of the arms 153a, 153b will be at the same height as the opposite side edges of the multi-stage gripper comb 140. In the embodiment shown in FIG. 11, upper surface 93a will be at the same height as the exposed side edge 156a (FIG. 9) of first carriage 156 (near gripper comb 126d), and upper surface 93b will be at the same height as the exposed side edge 156b (FIG. 9) of first carriage 156 (near gripper comb 126a).

Control unit 24 then operates first drive 128a to move multi-stage gripper comb 140 within the confines of the opposite arms 153a, 153b of first holder 153. In the embodiment shown in FIG. 11, upper surface 93a will be facing the exposed side edge 156a (FIG. 9) of first carriage 156, and upper surface 93b will be facing the exposed side edge 156b (FIG. 9) of first carriage 156. The control unit 24 then causes the locking mechanism to release first carriage 156 from support 157. Then control unit 24 controls the first pick and place mechanism 127a to retract first telescoping member 152a toward first trolley 151a. This retraction raises first holder 153 until the opposed arms 153a, 153b of first holder 153 engage the opposite side edges 156a, 156b of multi-stage gripper comb 140. At this stage of the process, first pick and place mechanism 127a has acquired multi-stage gripper comb 140.

The control unit 24 can continue to operate first telescoping member 152a to retract toward first trolley 151a and thereby cause first pick and place mechanism 127a to lift first holder 153 to a predetermined height above support 157 that will enable first holder 153 to clear any obstacles disposed between needle array 112 and the first testing station 150. The multi-stage gripper comb 140 that is captured between the arms 153a, 153b of the first holder 153 also will be lifted by this movement of the first holder. It is at this point that first pick and place mechanism 127a is ready to translate multi-stage gripper comb 140 in the direction of arrow 131 in FIG. 10 to the first testing station 150. Control unit 24 then causes first trolley 151a to move along first guideway 129a toward second stanchion 141b where the first testing station 150 is disposed.

In an alternative embodiment, the first drive 128a and the multi-stage gripper comb 140 can be left connected as a unit that is moved by the first pick and place mechanism 127a.

Figure 12:
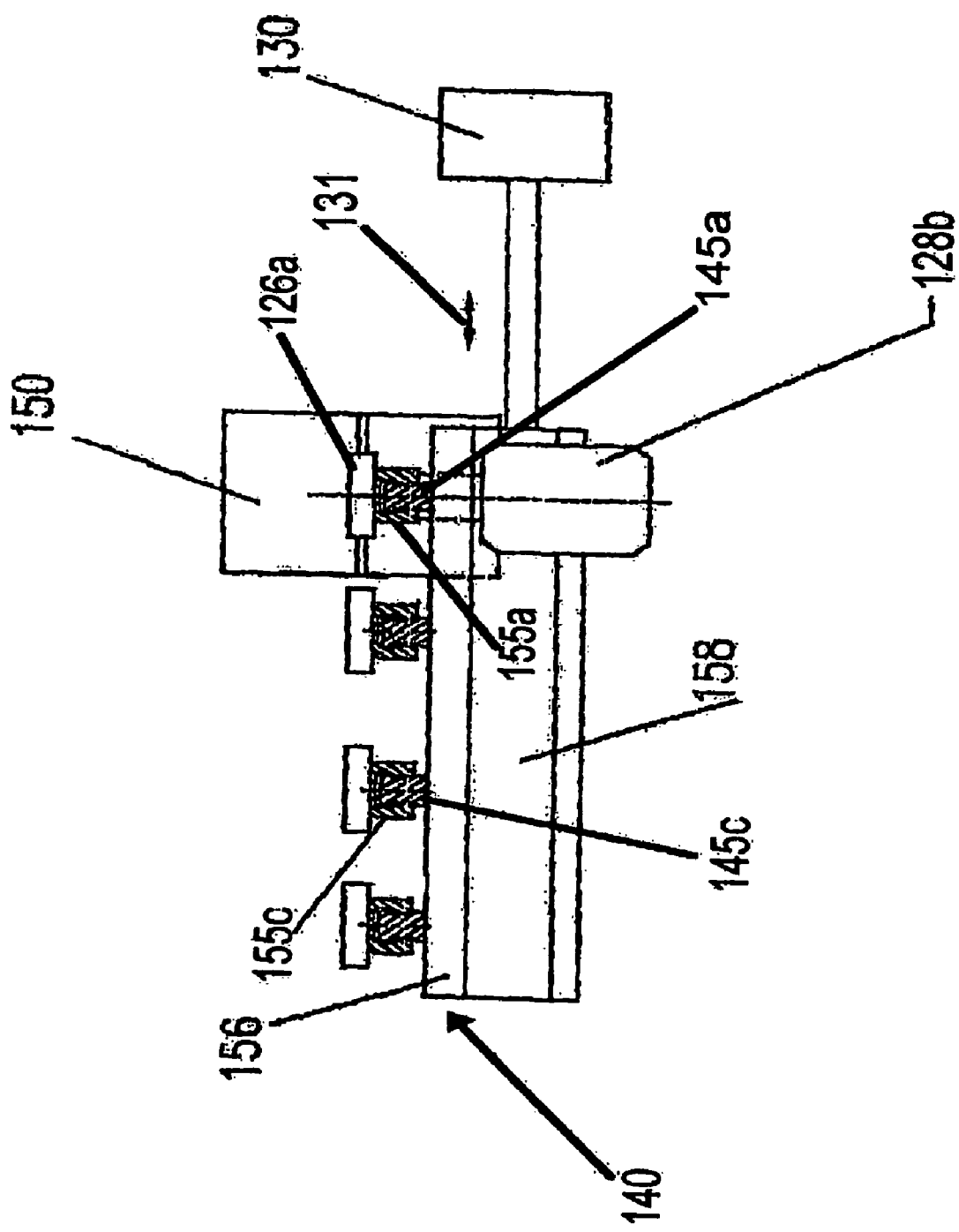
FIG. 12 schematically presents a front plan view of components (some shown in cross-section) of the embodiment of the apparatus of the present invention shown in FIGS. 8, 9, 10 & 11.

As shown schematically in FIGS. 10-12, a second drive unit 128b is disposed in front of the first testing station 150, and a third drive unit 130 is disposed to one side of the first testing unit 150. As shown in FIG. 12, a second carriage 158 is positioned in front of the first testing station 150 and has one side connected to the third drive unit 130. When the first multi-stage gripper comb 140 arrives at the first testing station 150 as schematically shown in FIG. 10, the control unit 24 causes the first trolley 151a to stop. Then the control unit 24 controls the release of the first multi-stage gripper comb 140 from the first pick and place mechanism 127a in a sequence that is essentially the opposite of the acquisition sequence.

The control unit 24 causes the first pick and place mechanism 127a to lower the multi-stage gripper comb 140 onto the second carriage 158 and causes a locking mechanism (not shown) to lock the first carriage 156 to the upper edge of the second carriage 158. The control unit 24 then causes the first pick and place mechanism 127a to lower the holder 153 until its upper surfaces 93a, 93b are opposed to the side edges 156a, 156b of the first carriage 156. The control unit 24 then operates the second drive unit 128b to move the multi-stage gripper comb 140 in the direction of arrow 137 in FIG. 10. This movement causes the multi-stage gripper comb 140 to be slid out from between the opposed upper surfaces 93a, 93b of the arms 153a, 153b of the first holder 153. At this point, the first pick and place mechanism 127a has released the multi-stage gripper comb 140 in front of the first testing station as shown in FIG. 10 for example.

As shown schematically in FIG. 11 for example, the control unit 24 causes the first trolley 151a to move back toward the first stanchion 141a and the extended needle array 112. In this way, first pick and place mechanism 127a can be prepared for acquiring and moving another multi-stage gripper comb 140 with a new batch of end-aligned fiber samples.

Upon being installed at the first testing station 150, the control unit 24 can cause the individual gripper combs 126a, 126b, 126c, 126d of the multi-stage gripper comb 140 to be moved selectively along each of two orthogonal axes relative to the testing station 150. In FIG. 12, one of these axes extends into and out of this drawing. This is the axis of movement that applies to the separate movements of each of the individual gripper combs 126a, 126b, 126c, 126d and is the same direction that is indicated by the arrows that are designated by the numerals 136 and 137 in FIG. 10. The control unit 24 also can operate the third drive unit 130 to move the multi-stage gripper comb 140 along the other of the two orthogonal axes relative to the testing station 150. This other orthogonal axis is indicated by the arrows that are designated by the numeral 131 in FIG. 12 for example.

As shown schematically in FIG. 10 for example, second drive 128b defines its own central axis 139b and is configured to translate each individual gripper comb 126a, 126b, 126c, 126d selectively toward and away from the testing station 150 by a predetermined distance under the instructions of the control unit 24. As shown in FIG. 10 for example, each individual gripper comb 126a, 126b, 126c and 126d of the multi-stage gripper comb 140 is denoted by a central axis 138a, 138b, 138c and 138d, respectively. As shown in FIG. 12 for example, the control unit 24 (not shown in FIG. 12) causes the third drive 130 to move the second carriage 158 in the direction indicated by arrow 131. Since second carriage 158 is attached to multi-stage gripper comb 140, it also moves in the direction indicated by arrow 131 such that the first gripper comb 126a is moved into position to use the testing station 150. This condition of readiness to use the testing station 150 is schematically indicated in FIG. 10 by the coincident alignment of the central axis 138a of the first gripper comb 126a with the central axis 139b of the second drive 128b.

Once the readiness condition has been attained by the first gripper comb 126a, then the control unit 24 causes the locking mechanism to unlock the base 155a from the pedestal 145a. Then the control unit 24 instructs the second drive unit 128b to move only the first gripper comb 126a along tracks (not shown), towards the testing station 150 in the direction indicated by the arrow designated by the numeral 136 in FIG. 10 for measurement of the various characteristics of the end-aligned sample 46. Accordingly, the multi-stage gripper comb 140 is configured so that by sliding one of the individual gripper combs 126 along its central axis 138, that individual gripper comb 126 will become misaligned with the remaining aligned individual gripper combs in the multi-stage gripper comb 140.

After the completion of the testing for the first individual gripper comb 126a as described above in relation to FIG. 1 for example, the control unit 24 causes the second drive 128b to move the single gripper comb (e.g., 126a) along tracks (not shown), away from the testing station 150 in the direction indicated by the arrow designated by the numeral 137 (FIG. 10) until the individual gripper comb (e.g., 126a) is realigned with the other gripper combs (e.g., 126b, 126c, 126d) in the set that forms the multi-stage gripper comb 140. The control unit 24 then causes the locking mechanism to lock the first base 155a to the first pedestal 145a.

The control unit 24 then causes the third drive 130 to move the multi-stage gripper comb 140 in the direction of arrow 131 in FIG. 10 by a sufficient distance such that the second gripper comb 126b is moved into position to use the testing station 150. The condition of readiness to use the testing station will occur when the central axis 138b of the second gripper comb 126b becomes aligned with the central axis 139b of the second drive 128b. Once the readiness condition has been attained by the second individual gripper comb 126b, then the control unit 24 causes the locking mechanism to unlock the base 155b from the pedestal 145b. The control unit 24 then instructs the second drive 128b to move the second gripper comb 126b in the direction indicated by the arrow designated by the numeral 136 towards the testing station 150 for testing of the end-aligned sample 46 that is carried by the second gripper comb 126b.

The foregoing process desirably can be repeated until all the gripper combs 126 within the set comprising the multi-stage gripper comb 140 have presented their end-aligned samples 46 to be tested. Depending on the nature of the first testing station 150, the individual gripper combs 126 in the multi-stage gripper comb 140 may still contain the end-aligned samples 46 or the individual gripper combs 126 may have been emptied of the end-aligned samples 46 as a result of the testing that was performed at the first testing station 150. Upon completion of the process at the first testing station 150, then the multi-stage gripper comb 140 comprising the complete set of gripper combs 126a, 126b, 126c, 126d can be removed to a second testing station or temporarily to a change over station. As shown schematically in FIGS. 13-15, this second testing station or a change over station can be disposed near a third stanchion 141c.

Figure 14:
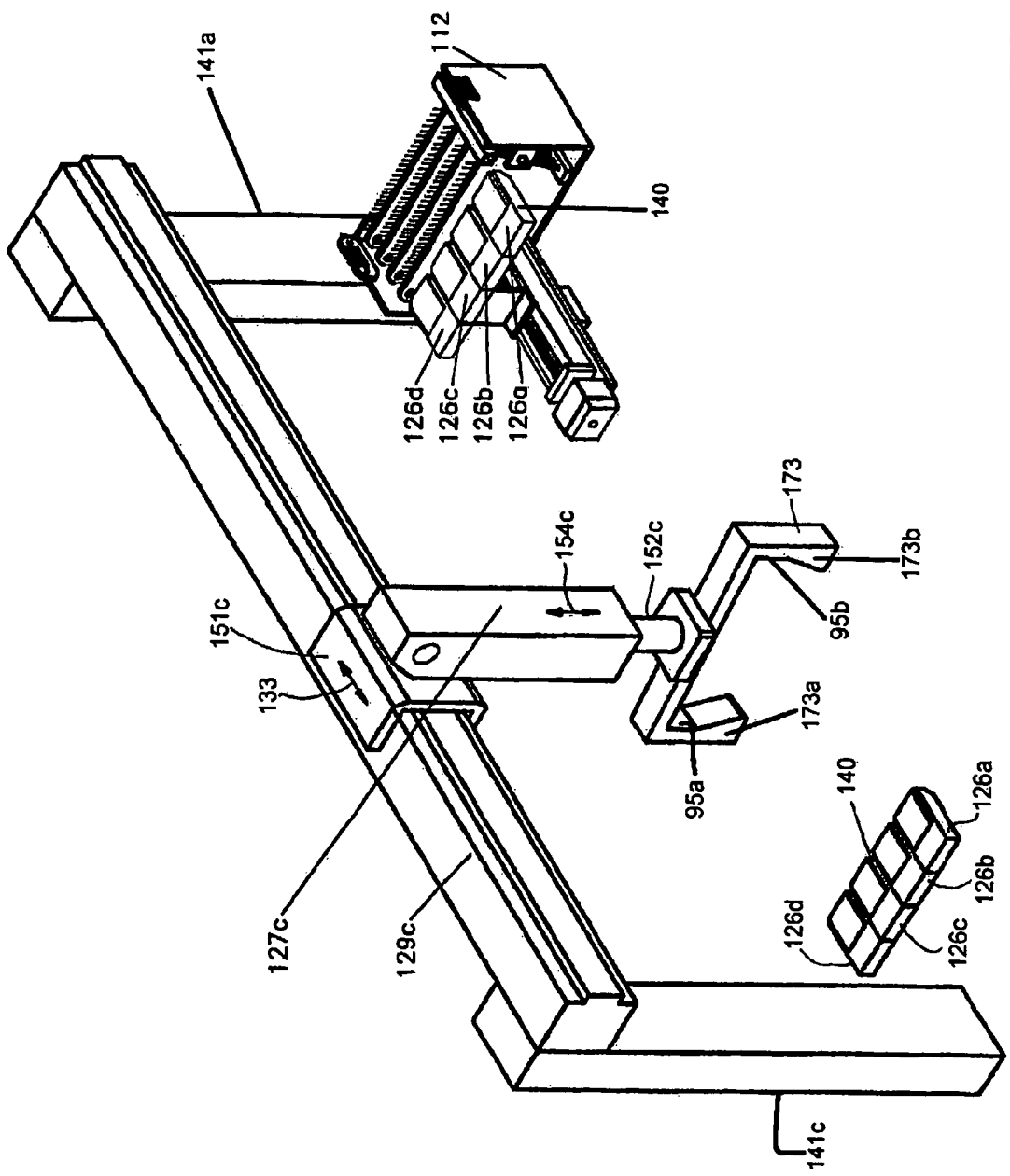
FIG. 14 schematically presents an elevated perspective view of components of the embodiment of the apparatus of the present invention shown in FIGS. 8 & 10.

As shown schematically in FIGS. 8, 10 and 14, different pick and place mechanisms 127a, 127b and 127c can be carried by different sections of guideways 129a, 129b, 129c that can be oriented to extend in different linear directions. The different linear directions of these different sections of guideways 129a, 129b, and 129c are indicated respectively in FIG. 10 by the arrows designated by the numerals 131, 132 and 133. Moreover, these differently directed sections of guideways 129a, 129b, 129c can be connected at nodes where the direction of the linear run of the guideways 129 changes from one direction such as the direction that is indicated by the arrow designated by the numeral 131 in FIG. 10 to another direction such as the direction that is indicated by the arrow designated by the numeral 132. At each of these nodes, the guideways 129 can be connected to a common upright stanchion 141a, 141b, 141c such as shown schematically in FIG. 15 for example.

Figure 13:
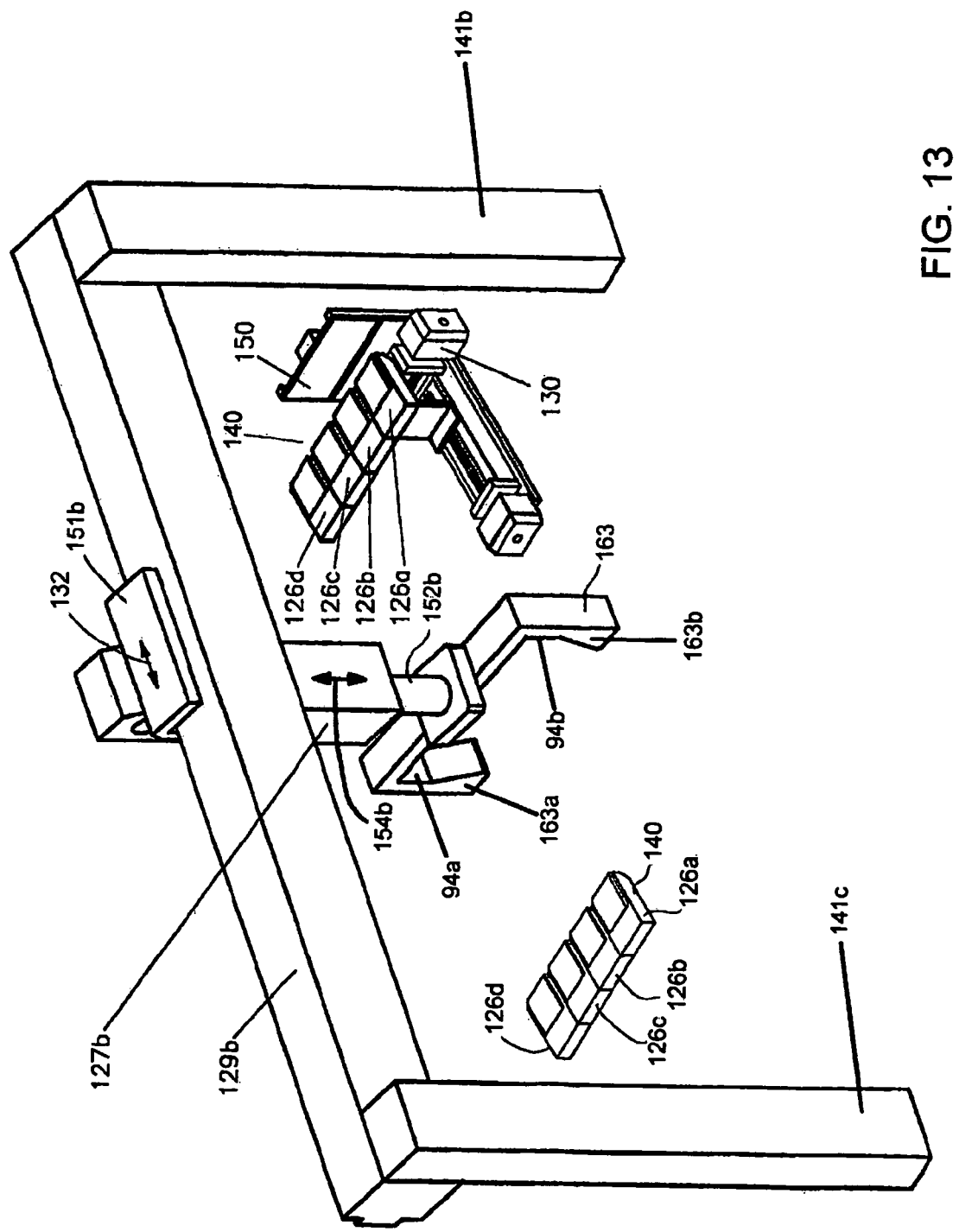
FIG. 13 schematically presents an elevated perspective view of components of the embodiment of the apparatus of the present invention shown in FIGS. 8 & 10.

As schematically shown in FIG. 13, the set 140 of gripper combs 126a, 126b, 126c, 126d can be acquired by the second holder 163 of the second pick and place mechanism 127b from in front of the first testing station 150. To effect this acquisition, the control unit 24 will provide instructions to the second trolley 151b, the second telescoping member 152b, the second drive unit 128b and the third drive unit 130 that essentially reverse the order of steps that were carried out by the first pick and place mechanism 127a to install the multi-stage gripper comb 140 onto the second carriage 158, but instructing the second pick and place mechanism 127b instead of the first pick and place mechanism 127a.

Once the multi-stage gripper comb 140 has been acquired by the second holder 163 of the second pick and place mechanism 127b, then the control unit 24 instructs the second trolley 151b to move the second pick and place mechanism 127b from in front of the first testing station 150 to a change over station near a third stanchion 141c. The control unit 24 can cause the second pick and place mechanism 127b to park the first set 140 of multiple gripper combs 126a, 126b, 126c, 126d at the change over station that exists at this node at the third stanchion 141c. Though not shown in FIG. 13, another drive unit 128 with associated pedestal 147 and support 157 similar to what is shown in FIG. 9 can be disposed at the third stanchion 141c to receive the first multi-stage gripper comb 140 from the second pick and place mechanism 127b.

The control unit 24 can effect the parking of the multi-stage gripper comb 140 at the third stanchion 141c by providing instructions to the second trolley 151b, the second telescoping member 152b, and the drive unit (not shown but similar to first drive unit 128a) at the third stanchion 141c, that essentially reverses the order of steps that were carried out by the first pick and place mechanism 127a to acquire the multi-stage gripper comb 140 from the first drive unit 128a, but instructing the second pick and place mechanism 127b instead of the first pick and place mechanism 127a.

As schematically shown in FIG. 14, the set of gripper combs 126a, 126b, 126c, 126d can be acquired by the holder 173 of the third pick and place mechanism 127c and moved from the change over station at the third stanchion 141c to the extended needle array 112 at the first stanchion 141a. The acquisition steps are similar to the prior description of the acquisition performed by the first pick and place mechanism 127a from the first drive unit 128a in front of the extended needle array 112. Once the acquisition of the multi-stage gripper comb 140 is accomplished by the third pick and place mechanism 127c, the control unit 24 then causes the third trolley 151c to move the third pick and place mechanism 127c to the first drive unit 128a in front of the extended needle array 112.

Then the control unit 24 instructs the third pick and place mechanism 127c to transfer the first set 140 of gripper combs 126a, 126b, 126c, 126d to the support 157 (shown in FIG. 9) of the first drive unit 128a by essentially following the reverse order of the steps described above for acquisition of the multi-stage gripper comb 140 by the first pick and place mechanism 127a. Once the multi-stage gripper comb 140 is transferred into this position in front of the needle array 112 by the third pick and place mechanism 127c, then the control unit 24 can cause the third telescoping member 152c (FIG. 14) to lower the first carriage 156 onto the support 157 (FIG. 9). The control unit 24 then causes the locking mechanism to lock the first carriage 156 to the support 157. The first carriage 156 is thereby held at a fixed height while the control unit 24 causes the third telescoping member 152c to lower the third holder 173 until the multi-stage gripper comb 140 is released from the third pick and place mechanism 127c. The control unit 24 then instructs the third trolley 151c to move away from the first stanchion 141a and toward the third stanchion 141c.

The control unit 24 then instructs the first drive unit 128a to move the set of gripper combs 126a, 126b, 126c, 126d to perform the process described above so as to transform a new set of non-end-aligned samples 43 into a new set of end-aligned samples 46.

As shown schematically in FIG. 8, a separate multi-stage gripper comb 140, 240, 340 is desirably provided for each node in the system. In this way, when a first set 140 of gripper combs 126a, 126b, 126c, 126d is in the process of preparing end-aligned samples 46, a second set 240 of gripper combs 226a, 226b, 226c, 226d can be disposed to present the end-aligned samples for testing by a testing station 150. Still a third set 340 of empty gripper combs 326a, 326b, 326c, 326d can be disposed to wait at a change over station that is provided along the route mapped out by the guideways 129 that carry the pick and place mechanisms 127. When the preparation of end-aligned samples 46 in the first multi-stage gripper comb 140 is complete, then the control unit 24 can be programmed to move the first set 140 of gripper combs 126a, 126b, 126c, 126d to the testing station 150 and the second multi-stage gripper comb 240 to the change over station, while yet a third set 340 of empty gripper combs 326a, 326b, 326c, 326d is moved from the change over station to the extended needle array 112 for preparation of end-aligned fiber samples 46. In this way, each separate set of multiple gripper combs 126, 226, 326 occupies a different node or section of the guideways 129 that are served by the respective pick and place mechanisms 127, and a more efficient use of the system's resources is effected.

Moreover, it will be appreciated that the same or similar system of guideways 129 and pick and place mechanisms 127 can be used to effect automatic movement of the single gripper comb 26 embodiments, one example of a single gripper comb 26 embodiment being shown schematically in FIG. 1 for example.

Figure 16:
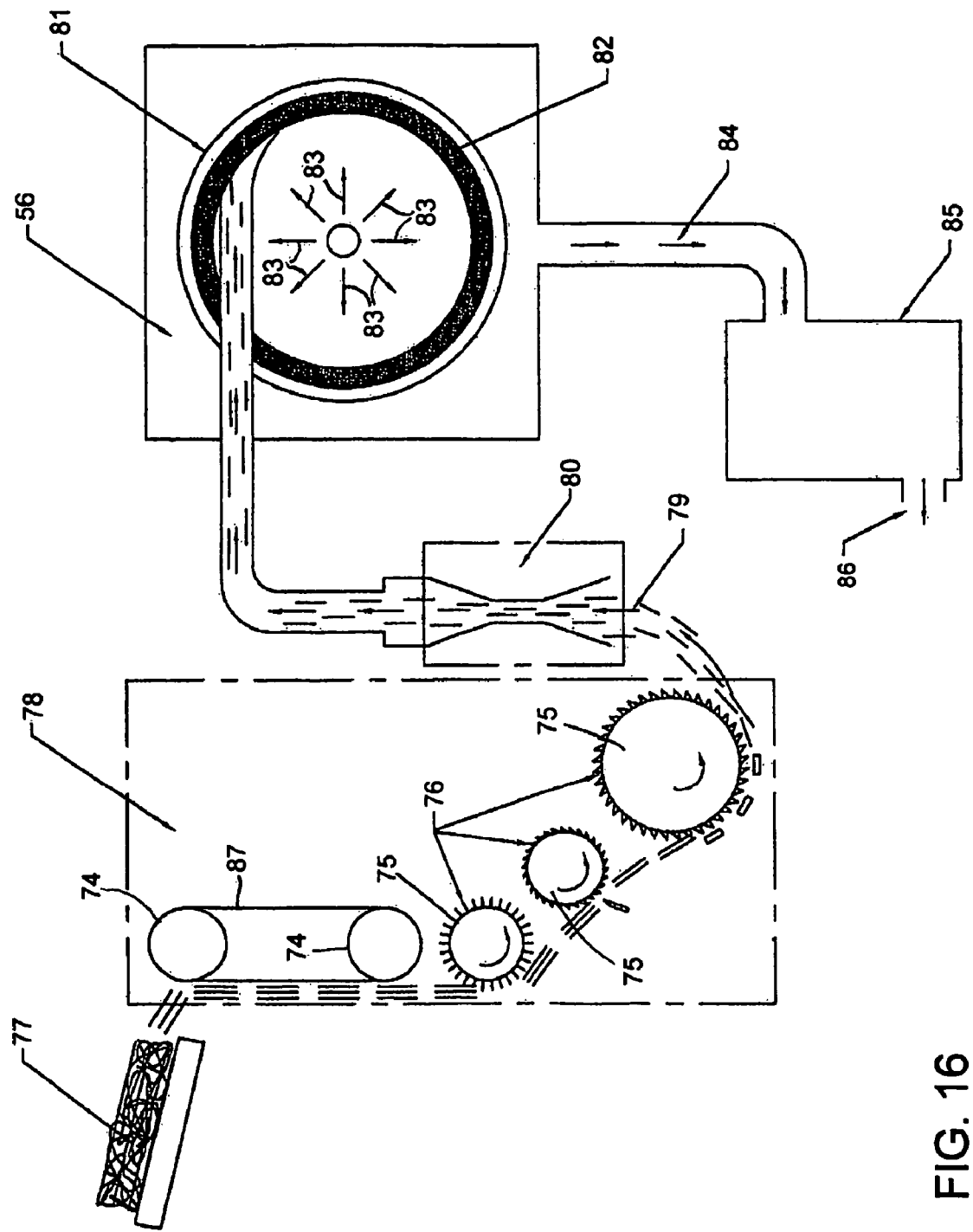
FIG. 16 is a schematic representation of an optional component of an embodiment of the present invention taken from a cross-sectional viewpoint.

Before placement of the fiber material on the array 12 (or extended array 112) of needles 18 to provide the starting fiber assembly 43 for preparation of the end-aligned fiber sample 46, a separate device such as a sliver unit 56 may be employed to prepare the fibrous material into the starting fiber assembly 43 of fibers aligned side-by-side in a parallel fashion. As shown schematically in FIG. 1 for example, a sliver unit 56 as shown in FIG. 16 and explained below can be provided. This sort of a sample preparation may be necessary only in the case of unopened fiber material and can be used as an optional device.

In a presently preferred arrangement shown schematically in FIG. 16 for example, this sliver preparation unit 56 desirably includes an aeromechanical individualizer, which produces a sliver from which can be extracted fiber assemblies 43. Each extracted fiber assembly 43 that is extracted from the sliver is composed of fibers that are both individualized and oriented with their lengths parallel to each other. In the embodiment shown, the aeromechanical individualizer includes a set of roller pairs 74. The different roller pairs 74 rotate a belt 87 at progressively increased speed to perform a drafting action that begins the process of rendering the fibers with their lengths parallel to each other. This fiber assembly 43 is thus "parallelized" and can then be placed manually on the array 12 of needles 18 held in combs 17.

As shown in FIG. 16, the individualizer includes a sequence of rollers 75 that are configured to act as a feed cum opening device. Rollers 75 operate to thoroughly open and render the fibers (indicated schematically by the short parallel lines) parallel to each other along their lengths. As schematically shown in FIG. 16, each feed cum opening roller 75 is covered with suitable wires 76 that help to open the fibers and transfer the fibers. A linearly arranged fiber mass 77 is fed to this arrangement 78 of rollers 74, 75. After this fiber mass 77 is processed through this arrangement 78 of rollers 74, 75, the fibers are fed to an air stream 79. A motor provides suction that creates the air stream 79 carrying the fibers. The air carries the fibers through a sensing channel in a laterally elongated acceleration/deceleration gas flow nozzle 80 such as a venturi and deposits the fibers in a sliver preparation device 56.

As embodied herein and shown in FIG. 16 for example, the sliver preparation device 56 includes a rapidly rotating chamber 81, which conveniently can be formed in the shape of a cylinder but could be any shape. The air stream carries the fibers 82 to the outer edges of the chamber 81 where the fibers 82 are deposited and retained. As the chamber 81 is rapidly rotated, the centrifugal force (schematically indicated by the outwardly radiating arrows designated by the numeral 83) that is generated by this rotation of chamber 81 pushes the fibers 82 to the outer edges of chamber 81. The air carrying the fibers 82 is further drawn by suction from the chamber 81 through a duct 84 into a suction box 85. The air ultimately passes out of the device 56 through an outlet 86 from the suction box 85. As the process continues, more and more fibers 82 are accumulated until a stage is reached when the accumulated fibers 82 resembles a sliver that is suitable for placement in the array 12 of needles 18 that is formed by the fiber combs 17.

If sliver preparation is not desired, then the chamber 81 is not rotated. In this optional mode of operation, the air stream 79 carries the fibers 82 to the suction box 85, where the fibers 82 are retained while the air escapes via the outlet duct 86.

Alternatively, other embodiments of a sliver unit 56 can be provided. One such alternative embodiment of the sliver unit 56 is another embodiment of an aeromechanical individualizer suitable for incorporation into this embodiment of the invention. Such an aeromechanical individualizer is disclosed in U.S. Pat. No. 5,929,460, which is commonly owned and hereby incorporated herein by this reference. Another alternative embodiment of the sliver unit 56 includes a set of roller pairs, with the different roller pairs rotating at progressively increased speed to perform a drafting action and forming a parallelised fiber assembly that then can be placed on the needle arrays. This sort of a sample preparation may be necessary only in the case of unopened fiber material and is used as an optional device.

While several presently preferred embodiments of the invention have been described using specific terms, such description is for illustrative purposes only, and it is to be understood that changes and variations may be made without departing from the spirit or scope of the following claims.

What is claimed is:

1. A method of processing a fiber sample taken from a supply of fibers, the steps comprising:

providing an assembly of elongated fibers disposed side-by-side and arranged with the lengths of the individual fibers extending in a direction that is generally parallel to each other;

disposing said fiber assembly atop an array of aligned fiber combs including at least a first fiber comb disposed parallel to and in front of a second fiber comb;

moving the open jaws of a gripper comb toward said fiber assembly until said gripper comb is disposed at a first distance from said first fiber comb and at least some of the fibers of said fiber assembly project into said jaws of said gripper comb;

closing said jaws of said gripper comb to hold said fibers projecting into said jaws of said gripper comb;

moving said closed jaws of said gripper comb away from said fiber assembly;

opening said jaws of said gripper comb to release said fibers projecting into said jaws of said gripper comb;

suctioning away said released fibers from said jaws of said gripper comb;

determining whether the fibers remaining atop said array of fiber combs has attained the end-aligned condition;

upon determining the absence of the end-aligned condition, moving the open jaws of the gripper comb toward said fiber assembly until said gripper comb is disposed at a second distance from said first fiber comb that is less than said first distance and at least some of the remaining fibers of said fiber assembly project into said jaws of said gripper comb;

closing said jaws of said gripper comb to hold said fibers projecting into said jaws of said gripper comb;

moving said closed jaws of said gripper comb away from said fiber assembly;

opening said jaws of said gripper comb to release said fibers projecting into said jaws of said gripper comb;

suctioning away said released fibers from said jaws of said gripper comb;

determining whether the end-aligned condition of the fibers remaining atop said array of fiber combs has been attained;

upon determining that the end-aligned condition in the fibers remaining atop said array of fiber combs has been attained, removing said first fiber comb from said array of fiber combs;

moving the open jaws of the gripper comb toward said fiber assembly until said gripper comb is disposed at a third distance from said second fiber comb that permits the ends of the remaining fibers carried by said second fiber comb to project into said jaws of said gripper comb; and
closing said jaws of said gripper comb to hold said fibers projecting into said jaws of said gripper comb, said fibers projecting into said jaws of said gripper comb composing said sample of end-aligned fibers.

2. A method as in claim 1, further comprising the steps of:
moving said closed jaws of said gripper comb with said sample of end-aligned fibers away from said array of fiber combs; and
transferring said end-aligned fiber sample to a testing station.

3. A method as in claim 2, further comprising the step of:
at the testing station, determining the short fiber content of the end-aligned fiber sample.

4. A method as in claim 1, wherein said step of providing an assembly of elongated fibers disposed side-by-side and arranged with the lengths of the individual fibers extending in a direction that is generally parallel to each other includes:
preparing a sliver from the supply of fiber from which the sample is to be composed.

5. A method as in claim 1, wherein said step of providing an assembly of elongated fibers disposed side-by-side and arranged with the lengths of the individual fibers extending in a direction that is generally parallel to each other includes:
using an aeromechanical individualiser to prepare a sliver from the supply of fiber from which the sample is to be composed.

6. A method as in claim 5, wherein said step of using an aeromechanical individualiser to prepare a sliver includes:
introducing fibers into a rapidly rotating, perforated chamber with a channel defined around its inner surface and accumulating fibers in said channel until said channel contains said sliver.

7. A method as in claim 1, wherein said step of determining whether the end-aligned condition of the fibers remaining atop said array of fiber combs has been attained includes:
scanning the edges of the remaining fibers in said fiber assembly projecting from said first fiber comb.

8. A method as in claim 7, wherein said step of scanning the edges of the remaining fibers in said fiber assembly projecting from said first fiber comb includes:
using an optical scanner.

9. A method as in claim 1, further comprising the steps of:
measuring the proportion of short fibers in said end-aligned sample by successively moving said gripper comb containing said end-aligned fiber sample a predetermined short distance away from said array of fiber combs and using an optical sensor to measure the optical mass of fibers at said predetermined short distance relative to said array of fiber combs.

10. An apparatus for aligning one end of a fiber sample before testing, the sample including an assembly of elongated fibers disposed side-by-side and arranged with the lengths of the individual fibers extending in a direction that is generally parallel to each other, the apparatus comprising:
an array of aligned fiber combs, said array of fiber combs including at least a first fiber comb and a second fiber comb disposed parallel to and behind said first fiber comb, said array of fiber combs being configured to receive the fiber sample resting with the direction of elongation of the fiber strands in said sample generally disposed transversely to the parallel direction of said first and second fiber combs;
a gripper comb disposed in front of said first fiber comb, said gripper comb having at least two jaws disposed in opposition to each other and configured to selectively move toward and away from each other to selectively close and open, respectively;
a first carriage carrying said gripper comb;
a first drive unit, said first drive unit being connected to said first carriage and configured to translate said first carriage and said gripper comb selectively toward and away from said array of fiber combs by pre-selected distances;
a suction device disposed to vacuum fibers from said jaws of said gripper comb when said drive unit translates said gripper comb to a location sufficiently distant from said array of fiber combs so as not to vacuum fibers from said array of fiber combs at the same time as fibers are being vacuumed from said jaws of said gripper comb; and
a detection device, said detection device including a sensor disposed between said first comb and said gripper comb, said detection device being configured to determine whether the end-aligned condition of the fibers remaining atop said array of fiber combs has been produced.

11. An apparatus as in claim 10, wherein said detection device includes:
a control unit connected to receive signals from said sensor and programmed to interpret signals received from said sensor to determine whether the end-aligned condition of the fibers remaining atop said array of fiber combs has been produced.

12. An apparatus as in claim 11, wherein said control unit is connected to said gripper comb, said first drive unit and said suction device and programmed to control operation of said gripper comb, said first drive unit and said suction device.

13. An apparatus as in claim 11 further comprising:
a frame supporting said array of fiber combs, one end of said first fiber comb being pivotally mounted with respect to said frame, said first fiber comb defining an elongated slot; and
a vertically translatable piston rod having one end pivotally connected to ride within said slot of said first fiber comb.

14. An apparatus as in claim 10, further comprising:
a second drive unit carrying said first drive unit, said second drive unit being configured to translate said first drive unit, said first carriage and said gripper comb selectively toward and away from said array of fiber combs.

15. An apparatus as in claim 10, further comprising:
a support platform disposed beneath said array of fiber combs, said gripper comb and said first drive unit.

16. An apparatus as in claim 15, wherein said suction device comprises a collection chamber disposed beneath said support platform and configured for collection of fibers vacuumed away from said jaws of said gripper comb.

17. An apparatus as in claim 15, further comprising:
an aeromechanical individualizer for preparing a fiber sample for reception by said array of fiber combs, said aeromechanical individualizer being connected to said support platform.

18. An apparatus for aligning at substantially the same time, one end of each of at least two fiber samples before testing, each of the samples including an assembly of elongated fibers disposed side-by-side and arranged with the lengths of the individual fibers extending in a direction that is generally parallel to each other, the apparatus comprising:
an array of aligned fiber combs, said array of fiber combs including at least a first fiber comb and a second fiber comb disposed parallel to and behind said first fiber comb, said array of fiber combs being configured to receive at least two discrete fiber samples, each fiber sample resting with the direction of elongation of the fiber strands in said sample generally disposed transversely to the parallel direction of said first and second fiber combs;

at least a first gripper comb and a second gripper comb disposed adjacent said first gripper comb, said gripper combs being connected to move in unison, each said gripper comb being disposed in front of said first fiber comb, each said gripper comb having at least two jaws disposed in opposition to each other and configured to selectively move toward and away from each other to selectively close and open, respectively; and a first carriage carrying said gripper combs; and a first drive unit, said first drive unit being configured to translate said first carriage and said gripper combs together selectively toward and away from said array of fiber combs by pre-selected distances.

19. An apparatus as in claim 18, further comprising:

a suction device disposed to vacuum fibers from said jaws of said gripper combs when said first drive unit translates said gripper combs to a location sufficiently distant from said array of fiber combs so as not to vacuum fibers from said array of fiber combs at the same time as fibers are being vacuumed from said jaws of said gripper combs.

20. An apparatus as in claim 18, further comprising:

a detection device, said detection device including a sensor disposed between said first comb and said gripper combs, said detection device being configured to determine whether the end-aligned condition of the fibers remaining atop said array of fiber combs has been attained.

21. An apparatus as in claim 20, wherein said detection device includes:

a control unit connected to receive signals from said sensor and programmed to interpret signals received from said sensor to determine whether the end-aligned condition of the fibers remaining atop said array of fiber combs has been attained.

22. A system for automatically successively testing multiple fiber samples, each of the samples including an assembly of elongated fibers disposed side-by-side and arranged with the lengths of the individual fibers extending in a direction that is generally parallel to each other, the system comprising:

an aligning apparatus for aligning at substantially the same time, one end of each of at least two fiber samples before testing, each of the samples including an assembly of elongated fibers disposed side-by-side and arranged with the lengths of the individual fibers extending in a direction that is generally parallel to each other, said aligning apparatus including an array of aligned fiber combs, at least a first gripper comb and a second gripper comb, a first carriage and a first drive unit;

said array of fiber combs including at least a first fiber comb and a second fiber comb disposed parallel to and behind said first fiber comb, said array of fiber combs being configured to receive at least two discrete fiber samples, each fiber sample resting with the direction of elongation of the fiber strands in said sample generally disposed transversely to the parallel direction of said first and second fiber combs;

at least said first gripper comb being disposed adjacent said second gripper comb, said gripper combs being connected to move in unison, each said gripper comb being disposed in front of said first fiber comb, each said gripper comb having at least two jaws disposed in opposition to each other and configured to selectively move toward and away from each other to selectively close and open, respectively; and said gripper combs being carried by said first carriage, said first drive unit being configured to translate said first carriage and said gripper combs together selectively toward and away from said array of fiber combs by pre-selected distances;

a testing station disposed beside and spaced apart from said aligning apparatus;

a first pick and place mechanism disposed between said testing station and said aligning apparatus, said first pick and place mechanism being configured for acquiring said gripper combs together, said first pick and place mechanism being further configured for translating said gripper combs together from said aligning apparatus to said testing station, and said first pick and place mechanism being configured for positioning at least one of said gripper combs for testing at said testing station.

23. A system as in claim 22, further comprising:

a support platform disposed beneath said array of fiber combs, said gripper comb and said first drive unit;

a suction device having a collection chamber disposed beneath said support platform and configured for collection of fibers vacuumed away from said laws of each said gripper comb;

a holding station spaced apart from each of said suction device and said testing station, said holding station being disposed beside at least one of said aligning apparatus and said testing station;

a second pick and place mechanism disposed between said holding station and at least one of said testing station and said aligning apparatus, said second pick and place mechanism being configured for acquiring said gripper combs together, said second pick and place mechanism being further configured for translating said gripper combs together between said holding station and one of said aligining apparatus and said testing station, and said second pick and place mechanism being configured for positioning at least one of said gripper combs for holding at said holding station.

24. A system as in claim 22, wherein said first pick and place mechanism comprises:

a track disposed above at least said apparatus.

25. A system as in claim 24, wherein said first pick and place mechanism comprises:

a trolley configured and disposed to travel along said track;

a gripping arm configured to selectively grip and release said connected together gripper combs; and a telescoping member having one end connected to said trolley and an opposite end connected to said gripping arm, the distance between said opposite ends of said telescoping member being selectively variable.

26. A method of simultaneously processing multiple fiber samples from a supply of fibers, the steps comprising:

providing a plurality of discrete assemblies of elongated fibers disposed side-by-side and with each discrete assembly being arranged with the lengths of the individual fibers extending in a direction that is generally parallel to each other;

disposing each said discrete fiber assembly atop an array of aligned fiber combs including at least a first fiber comb disposed parallel to and in front of a second fiber comb;

simultaneously moving the open jaws of each of a plurality of gripper combs toward said fiber assemblies until each said gripper comb is disposed at a first distance from said first fiber comb and at least some of the fibers of one of said fiber assemblies project into said jaws of one of said gripper combs;

closing said jaws of each said gripper comb to hold at least some of the fibers projecting into said jaws of each said gripper comb;

simultaneously moving said closed jaws of each said gripper comb away from said fiber assemblies;

removing from said jaws of each said gripper comb said fibers projecting into said jaws of each said gripper comb;

determining whether the end-aligned condition of the fibers remaining atop said array of fiber combs has been attained;

upon determining the absence of the end-aligned condition, simultaneously moving the open jaws of the gripper combs toward said fiber assembly until each said gripper comb is disposed at a second distance from said first fiber comb that is less than said first distance and at least some of the remaining fibers of said fiber assemblies project into said jaws of at least one said gripper comb;

closing said jaws of at least one said gripper comb into which fibers are projecting to hold at least some of said fibers projecting into said jaws of said gripper comb;

moving said closed jaws of said gripper comb away from said fiber assembly;

removing from said jaws of said gripper comb said fibers projecting into said jaws of said gripper comb;

determining whether the end-aligned condition of the fibers remaining atop said array of fiber combs has been attained;

upon determining that the end-aligned condition in the fibers remaining atop said array of fiber combs has been attained, removing said first fiber comb from said array of fiber combs;

simultaneously moving the open jaws of the gripper combs toward said fiber assemblies until said gripper combs are disposed at a third distance from said second fiber comb that permits the ends of the remaining fibers carried by said second fiber comb to project into said open jaws of said gripper combs; and closing said jaws of said gripper comb to hold said fibers projecting into said jaws of said gripper combs, each discrete assembly of said fibers projecting into said jaws of said gripper combs composing a discrete sample of end-aligned fibers.

27. The method of processing fiber samples of claim 26, further comprising the step of:

transferring said end-aligned fiber samples to a testing station.

28. A method as in claim 27, further comprising the step of:

at the testing station, determining the short fiber content of a first one of the end-aligned fiber sample.

29. A method as in claim 28, further comprising the step of:

at the testing station, determining the short fiber content of a second one of the end-aligned fiber samples.

* * * * *